(12) United States Patent
Lewin et al.

(10) Patent No.: US 8,912,129 B2
(45) Date of Patent: Dec. 16, 2014

(54) METHOD FOR THE DETERMINATION OF THE DNA METHYLATION LEVEL OF A CPG POSITION IN IDENTICAL CELLS WITHIN A TISSUE SAMPLE

(75) Inventors: Joern Lewin, Berlin (DE); Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 1039 days.

(21) Appl. No.: 12/085,212

(22) PCT Filed: Nov. 17, 2006

(86) PCT No.: PCT/EP2006/011377
§ 371 (c)(1),
(2), (4) Date: May 19, 2008

(87) PCT Pub. No.: WO2007/057231
PCT Pub. Date: May 24, 2007

(65) Prior Publication Data
US 2009/0253584 A1    Oct. 8, 2009

(30) Foreign Application Priority Data
Nov. 17, 2005  (EP) .................................. 05090318

(51) Int. Cl.
*C40B 30/06*    (2006.01)
*C12Q 1/68*    (2006.01)

(52) U.S. Cl.
CPC ................................. *C12Q 1/6827* (2013.01)

USPC .......................................................... 506/10

(58) Field of Classification Search
None
See application file for complete search history.

(56) References Cited

U.S. PATENT DOCUMENTS

| 2005/0130170 A1 | 6/2005 | Harvey et al. |
| 2005/0221314 A1 * | 10/2005 | Berlin et al. ................... 435/6 |

FOREIGN PATENT DOCUMENTS

WO    WO 2005/040421 A2    5/2005

OTHER PUBLICATIONS

Nakayama (Sep. 2003) American Journal of Pathology vol. 163 pp. 923 to 933.*
Zhang et al., "Insensitivity to Transforming Growth Factor-Beta Results from Promoter Methylation of Cognate Receptors in Human Prostate Cancer Cells (LNCaP)," Molecular Endocrinology, 19(9):2390-9 (2005).

(Continued)

*Primary Examiner* — Christian Boesen
(74) *Attorney, Agent, or Firm* — Kriegsman & Kriegsman

(57) ABSTRACT

Aspects of the present invention relate to the determination of the DNA methylation level at one or more CpG position within cells of a defined type in a tissue sample. This methylation level is deduced from the total DNA methylation level of all cells of the sample and from the content of said cells of interest. In aspects of the invention, the cell content is determined by means of histopatholoy, staining methods, antibodies, expression analysis or DNA methylation analysis.

17 Claims, 5 Drawing Sheets

(56) References Cited

OTHER PUBLICATIONS

Nakayama et al., "Hypermethylation of the Human Glutathione S-Transferase-Pi Gene (GSTP1) CpG Island Is Present in a Subset of Proliferative Inflammatory Atrophy Lesions but Not in Normal or Hyperplastic Epithelium of the Prostate," American Journal of Pathology, 163(3):923-33 (2003).

De Capoa et al., "DNA demethylation is directly related to tumor progression: Evidence in normal, pre-malignant and malignant cells from uterine cervix samples," Oncology Reports, 10(3):545-9 (2003).

Hernandez-Blazquez et al., "Evaluation of global DNA hypomethylation in human colon cancer tissues by immunohistochemistry and image analysis," Gut, 47(5):689-93 (2000).

Habib et al., "DNA Global Hypomethylation in EBV-Transformed Interphase Nuclei," Experimental Cell Research, 249(1):46-53 (1999).

Johnson et al., "Tissue- and Cell-specific Casein Gene Expression," The Journal of Biological Chemistry, 258(17):10805-11 (1983).

* cited by examiner

SEQUENCE LISTING

<160> NUMBER OF SEQ ID NOS: 40

<210> SEQ ID NO 1
<211> LENGTH: 356
<212> TYPE: DNA
<213> ORGANISM: Artificial Sequence
<220> FEATURE:
<223> OTHER INFORMATION: chemically treated genomic DNA (Homo sapiens)

<400> SEQUENCE: 1
tacccaatgc gaaacatact acttaggacc tcagtgggggg cgctccataa atgcttgtta    60
tccgcaaata aaaccactg gaaagccacg aaggaaacca gtaagatttc tcagtgttct    120
tttttctggt ttgtattgct gtgcatcctc aggcgatttc ctggctttct ctctcttagc    180
ttagagggat aacagccatg tctcctctgt ccctaagga cagaccttca tcgagtccca    240
cttagaatgc taaaactgcg ctctggtttg tctctctgag tatggcctct cccagcctgc    300
ccatatccgt cagactaatc acactaccac aaggcataca gcacatgccc ctctta    356

<210> SEQ ID NO 2
<211> LENGTH: 240
<212> TYPE: DNA
<213> ORGANISM: Artificial Sequence
<220> FEATURE:
<223> OTHER INFORMATION: chemically treated genomic DNA (Homo sapiens)

<400> SEQUENCE: 2
tactggattc ctgagttgtc aaaggatatt gctgaattcc tggtatcgcc aatgccgcct    60
gagacctcat tcatttcatt gtgaacttcc agcgatgtca acagaatatt ccatgagca    120 tccacctaat tggacggaaa atgcacatgg ttagacagcc agcagcataa tttccctatg    180
cagatcccgg acagaatgat gtcatgccat cacatgttgc atgttttacg agaaactgta    240

<210> SEQ ID NO 3
<211> LENGTH: 338
<212> TYPE: DNA
<213> ORGANISM: Artificial Sequence
<220> FEATURE:
<223> OTHER INFORMATION: chemically treated genomic DNA (Homo sapiens)

<400> SEQUENCE: 3
taaagtggca gttctgtttt catttctctg aacccaattc atttccgtta tttctaaatt    60
tttctctctt cttggtgtcc acttagggct acgcagcttg ctcctggcac gggcaccttg    120
aatctcctcc tcacacagat ggagaccatg cttgatttcc tgaacttgta gtaagaagaa    180
ggaaaacaca gcacgctgga gccaacaggt aggcgagaaa ccaggtaggc gagaaacacg    240
tttctcagtt atgcagccca gcgtcgagga aaaataacag caactctaca aaatcagaaa    300
tcagcgtcta aggactaatg agcagagaga aaagtcta    338

<210> SEQ ID NO 4
<211> LENGTH: 120
<212> TYPE: DNA
<213> ORGANISM: Artificial Sequence
<220> FEATURE:
<223> OTHER INFORMATION: chemically treated genomic DNA (Homo sapiens)

<400> SEQUENCE: 4
tagcttaccc ggtgatggcg tctctgtctc aggtgatgca taaggaacca cagcatgtga    60
ctatcaaaca ggtcagtttg gtgcaagcta tcttcatccc gctcccgctt gttcttctta    120

<210> SEQ ID NO 5
<211> LENGTH: 316
<212> TYPE: DNA
<213> ORGANISM: Artificial Sequence
<220> FEATURE:
<223> OTHER INFORMATION: chemically treated genomic DNA (Homo sapiens)

<400> SEQUENCE: 5

```
taagaggact gattaccagg ttgatagatt tccaagcctt ctgttgttct atactctctc    60
tttcctgcc tttcgccgag aggaatatcc gtgtttcctg aggatggggg tgaaaaaatg   120
tctatccaat aatgcttgaa ttataatttt ggtgacaaaa gttttctttt ggggaggggg   180
aaggaattta gaatgtttag atttcacttt tctctgttct tgctaaatgt gtgtgccggc   240
ataaagaaca gagctgatgg ctgtcagtta tacgccgctt tcagatgtcg aatgctctac   300
attgtctgta gactta                                                   316
```

<210> SEQ ID NO 6
<211> LENGTH: 196
<212> TYPE: DNA
<213> ORGANISM: Artificial Sequence
<220> FEATURE:
<223> OTHER INFORMATION: chemically treated genomic DNA (Homo sapiens)

<400> SEQUENCE: 6

```
tacaccatgc aggggcccct gcagaaggca ggcacctcca gctctgcaga gggcagcaca    60
gtggcccact gccttttatc acagctgtgg aaccaaatgg aaactggacg ccgtcacgga   120
aaacgatcag tctgcatgac gggcgcatgg aaaggaagcc tgacatttga aaacacgttt   180
cttccaaata tcttta                                                   196
```

<210> SEQ ID NO 7
<211> LENGTH: 225
<212> TYPE: DNA
<213> ORGANISM: Artificial Sequence
<220> FEATURE:
<223> OTHER INFORMATION: chemically treated genomic DNA (Homo sapiens)

<400> SEQUENCE: 7

```
tacacttgaa cagtcagcat gatgctatct tagcgagcat gtgactcttc aataggtcaa    60
ctaaacacca gggaagcagc tgcctcaggc catcgtgttg gttccccttc ctgtgttagg   120
agatggagga gtggagggt gatgataaaa tggaagctcc cgtgtcaaga gatcaggcaa   180
atggggagac tccgtgggat cctctgaaga atctacatgc acgta                   225
```

<210> SEQ ID NO 8
<211> LENGTH: 518
<212> TYPE: DNA
<213> ORGANISM: Artificial Sequence
<220> FEATURE:
<223> OTHER INFORMATION: chemically treated genomic DNA (Homo sapiens)

<400> SEQUENCE: 8

```
taccctttgt ttattgtgcc tctgcatcct acccagtaat tagcattggc agcttcatat    60
tgagcttttg ttttcataat tcttttgccc gcgatgacat aataaaggga atattgattc   120
aatcccaact cctcttggcc agaagcccac atcaaccaat aaaaaagaat tgctaattgc   180
agagtgcgct tgcccagctg aggcattgga gcagggcatt tgatagtgg ctggagggca   240
ggcagctcaa cctctaaacc cccctggtct gggcaccaag tcctgtcctg ggcacgggac   300
acagtcctcc agcgagacca aacccagctt ctctacagca ccaggaagaa ggcaagctgg   360
gccaccaggg cgcggcccca ggaaggaaaa tcctccatgg tcctgttgac agatgtggta   420
tcaaatgaat tgttctctgc ttagacacga ctttgatatt tattggttca aattgctcgg   480
ctgactcagt cttgcgtaag tctccctggt ccgtttta                           518
```

```
<210> SEQ ID NO 9
<211> LENGTH: 535
<212> TYPE: DNA
<213> ORGANISM: Artificial Sequence
<220> FEATURE:
<223> OTHER INFORMATION: chemically treated genomic DNA (Homo sapiens)

<400> SEQUENCE: 9
taatagcaat catagctctc atgtgtgccc tgtctgcagg ctacctggcg acatcagtgg      60
aggagggccc tctcccaggc taaacaggtg tttctctctt ttgagaggta tacctttaga     120
actccaaggt gagctgacca ttgcctgcaa atggcgtgtc cttacattcg tattatattt     180
tgcagaaaaa gcgtgaagtc atactaaata agtcaacaaa cgcttttaca actgggaaga     240
tgtctcaccc cccaaacatt ccgaaggaac agaccccagc agggacgtcg aatacaacct     300
cagtctcagt aaaaccctct gaagagaaga cttctgaaag caaaaagact tacaacagta     360
tcagcaaaat tgacaaaatg tcccgaatcg tattcccagt cttgttcggc actttcaact     420
tagtttactg ggcaacgtat ttgaataggg agccggtgat aaaaggagcc gcctctccaa     480
aataaccggc cacactccca aactccaaga cagccatact tccagcgaaa tggta          535

<210> SEQ ID NO 10
<211> LENGTH: 457
<212> TYPE: DNA
<213> ORGANISM: Artificial Sequence
<220> FEATURE:
<223> OTHER INFORMATION: chemically treated genomic DNA (Homo sapiens)

<400> SEQUENCE: 10
tacacatggg aaccatcgtt gtggatgaaa gcaaggctgt gccctcacgc gtgggatcca      60
tgccagctgt cactcaccct ccagcccagg tccctgtctg tcagctgggt atgtggcccg     120 gtggcccct cccagggtgc ttctgtgagg gtaatgtgaa gcgatgctgt ggacgccact      180
tagcacagga cttggcgcgc tttgaacgtg cagtagtaaa tgttagctgg gataattgtc     240
accatcctcc cacagccaca gatcctcagc gcccagtggg aggcatggag agagacgcac     300
atgtagacac ccccctcagg cagaatgaga cgcgtgggga aggcagctgg acacaagaca     360
cccacgtcca catgcagagc cacttagacg caggcacaag gcccgttggg gctggcgcac     420
actcacgttt gctcagcaga gcattttctg ggccta                              457

<210> SEQ ID NO 11
<211> LENGTH: 250
<212> TYPE: DNA
<213> ORGANISM: Artificial Sequence
<220> FEATURE:
<223> OTHER INFORMATION: chemically treated genomic DNA (Homo sapiens)

<400> SEQUENCE: 11
taggtttgga ggctctggtg ataaggggaa ctgcttccag cagaaaacaa agtcatagcg      60
gtgtgaaact gagaccaccc agttagggct ttacgtgcca cgagaaccac atgcagatga     120
ggtggttggg tgaaccgttc aaggtgctgt agctttcagg cgagtatgac tgaattgaca     180
tctccttgtt atgatcctgt agctgatggg actccgtcat ttccctggga cagaaccttg     240
gtttttcgta                                                             250

<210> SEQ ID NO 12
<211> LENGTH: 407
<212> TYPE: DNA
<213> ORGANISM: Artificial Sequence
```

```
<220> FEATURE:
<223> OTHER INFORMATION: chemically treated genomic DNA (Homo sapiens)

<400> SEQUENCE: 12
tacctttcca cgtattttcc tgtccagtca gatgaggaga gggaacagtc tgagagaacc      60
acgaaactgc caaacccagt gggcccgaat attccttcaa gatttcaaga aagccgacct     120
tgaggacggc cacggggcca actgcagtat ggacaagtcg ttcttgtagt tgcacagatg     180
gccattgaca aaacagccc tgcttgggtg actcctgagc cctgataccc gaatgagtat      240
gatcaagcgg tgatggacct ggatccggct gtgggagtgt cctgatgagc cctgggccag     300
cggaggtaag ccccaggctg gcggtcactc ctgggcactg gatttgaagc tcagggcctc     360 cttaccctg ccaccagaca tccactgcgt tttctccccc atttgta                   407

<210> SEQ ID NO 13
<211> LENGTH: 302
<212> TYPE: DNA
<213> ORGANISM: Artificial Sequence
<220> FEATURE:
<223> OTHER INFORMATION: chemically treated genomic DNA (Homo sapiens)

<400> SEQUENCE: 13
tagcaaactc ccagctcctg cctgacaagt tactgcctaa cccgtgactt atttcgggaa      60
tccctgacgc atttctttac cgtccctcat ttcaaagcac accatgccgg cagcacttgg     120
aggtggtatg tgctgggaaa ctgaccaaca gtttagtcag actgagtcac ttcaaggagg     180
ggagtggaga cagcagtggg tgccagatga cacggagctg tcggcttccg tgtgcatttt     240
cttttgatag tagccgtaga gaagttgtcc gccaggcagc cctcaatggg atttttcatt     300
ta                                                                   302

<210> SEQ ID NO 14
<211> LENGTH: 215
<212> TYPE: DNA
<213> ORGANISM: Artificial Sequence
<220> FEATURE:
<223> OTHER INFORMATION: chemically treated genomic DNA (Homo sapiens)

<400> SEQUENCE: 14
taacgtgtct atgcagggta ttatccgagc tgcctacttc ggtatctatg acaccgcaaa      60
gggaatgctt ccggatccca aggacactca catcgtcatc agctggatga ccacacagac     120
tgtcactgcc ttttctgggt tgacttccta ttcatttgac atcgttcgcc tctcgtgatg     180
attcagtcag ggcgcaaagt aactgacatc atgta                                215

<210> SEQ ID NO 15
<211> LENGTH: 306
<212> TYPE: DNA
<213> ORGANISM: Artificial Sequence
<220> FEATURE:
<223> OTHER INFORMATION: chemically treated genomic DNA (Homo sapiens)

<400> SEQUENCE: 15
taaatgggtc atgagccaga tggatttacg tagcctggat agaaacatga gaagtaactc      60
tttggcacca ccacagagtt ctggcgggca gccgcttagg gacactgctc acccacacag     120
ctggggatcg tgtcgttcca ctgtgccaag gcgttgggca cggactggca gtggagcgcc     180
gtggaaccct gaagcaggta tcccgggttg cactcgaatc ggacgatgga gccggcagaa     240
```

```
aactcagaac caattctcct tccgtatctg ggctcgggga cagagctgca ttgggtgtca    300
ctggta                                                                306

<210> SEQ ID NO 16
<211> LENGTH: 489
<212> TYPE: DNA
<213> ORGANISM: Artificial Sequence
<220> FEATURE:
<223> OTHER INFORMATION: chemically treated genomic DNA (Homo sapiens)

<400> SEQUENCE: 16
taatgttatt atgaactggg gcattttctc gttgcagcgc cccatattag gtcacatata     60
caaatgattt ttgacagatc cttccgctgc ccggctgtct tgtgtcatac aatgccaatg    120
ggactgaaaa tcctacgact gattctgccc cttgttgaga acgatagcag tttgaatttg    180
atttgtccat cttctgggat gatagtccat gttcccctttc agcaccgctg aatagacaat    240
gggcaccact tgtattcttt acagctcgtt cacctattat gatgatgatg tcattattca    300
cattattgct ctcattatta ttattatcat tacccggtga cctctgtcct ggggtggaac    360
tccccgtgac agatgggagc ttcgtttatc ggactgcttt atgctgcaca attcccctgc    420
cattctgagt ttatattgag acgggctgct tttggaacaa aggcagcctg atcacaattt    480
gtcagtgta                                                            489

<210> SEQ ID NO 17
<211> LENGTH: 139
<212> TYPE: DNA
<213> ORGANISM: Artificial Sequence
<220> FEATURE:
<223> OTHER INFORMATION: chemically treated genomic DNA (Homo sapiens)

<400> SEQUENCE: 17
taagtcttgc caaatttgat gccccctccgg aagctgttgc agccaagtta ggagtgaaga     60
gatgcacgga tcagatgtcc cttcagaaac gaagcctcat tgcggaagtc ctggtaactt    120 cttttctcctt tatttgtta                                                139

<210> SEQ ID NO 18
<211> LENGTH: 315
<212> TYPE: DNA
<213> ORGANISM: Artificial Sequence
<220> FEATURE:
<223> OTHER INFORMATION: chemically treated genomic DNA (Homo sapiens)

<400> SEQUENCE: 18
tacccaggga tctcaggcgc catgggctca acatcggggg gcaaagggat gccccagagc     60
agctcggcac aacaggagct ggcaaggatc ttagctcgtg gtcctgtggg atgcagcacg    120
ccatagtata agagcatcat tgcgatccca gccacaaagc taataaagac acaacacagt    180
gctggcaccg cataggagtc agtggtctcc gggtctctgt aaaaatacca aaggaacgtc    240
aaggcagcat tctcggtcaa gactatcgta taatatgcaa acattcgata tcgagtccgc    300
ccttccttga cgtta                                                     315

<210> SEQ ID NO 19
<211> LENGTH: 412
<212> TYPE: DNA
<213> ORGANISM: Artificial Sequence
<220> FEATURE:
<223> OTHER INFORMATION: chemically treated genomic DNA (Homo sapiens)
```

<400> SEQUENCE: 19

```
taagtggctc aaaagctgct ggcagaaaat acacgattcc gacagatgca cggtatcgag    60
ccctgcagcc aattgtgtta gagcaacaga accatgtgct gtttatgact cagtcataca   120
aggtgctggg gctcgctggc aaatttgcac ttataagtgg atatttagag ctaaacagaa   180
acgcctaata gctaagcagt cttctaaatt cgtctcaagg aaatagcccc cgggggtatc   240
agatgtttct aaatggagga gattaggcag tttgattgaa tgagaagcct cggtttaggt   300
gactgctcag aggatgcttt cggactattt tatttgagca aaaccgaggt cagggccagg   360
gcgaatattt gaagatgaag taagttttgg aatccgattt gaagagagtg ta           412
```

<210> SEQ ID NO 20
<211> LENGTH: 380
<212> TYPE: DNA
<213> ORGANISM: Artificial Sequence
<220> FEATURE:
<223> OTHER INFORMATION: chemically treated genomic DNA (Homo sapiens)

<400> SEQUENCE: 20

```
taaacaattt ttctgagaaa cgaaccacta cctcctatag catagactaa gttttgaagg    60
cacattctgg aaacagtgta agggctgtgg cggtcagtgg cacacctcgg aggcaggtgc   120
ggctcccttt ggacacaggt ggggtcaggc gcctccagtg gtgggaggtc ctctccactt   180
ctgcccatgg ttctcaccac aggcaccatc aaagctcaag tctgttcaga ttcgccctg   240 ttacgtgtag gttctgtctc tgtcacactc tctaatggac gcaaagtaga gctattgatt   300
ttgagtgatg atgctgtgtt cattctgttt gctgaattta tttactgtaa atggataagt   360
aaatgactgg taaatactta                                              380
```

<210> SEQ ID NO 21
<211> LENGTH: 173
<212> TYPE: DNA
<213> ORGANISM: Artificial Sequence
<220> FEATURE:
<223> OTHER INFORMATION: chemically treated genomic DNA (Homo sapiens)

<400> SEQUENCE: 21

```
taggcccggg agcaccaggg ggagggaggc aggagggcca ccgtgggtgc gggcctggcg    60 ccggggctcag cccgcggggg ccgcgtgggc ggggacgggg cgtcttgtcg cgggcacctg   120
tgcgcgtggg cgggcgcgca ctcgccagcg ctttgttcgt gaccggcctt tta           173
```

<210> SEQ ID NO 22
<211> LENGTH: 182
<212> TYPE: DNA
<213> ORGANISM: Artificial Sequence
<220> FEATURE:
<223> OTHER INFORMATION: chemically treated genomic DNA (Homo sapiens)

<400> SEQUENCE: 22

```
taaagagctt gagaaagttc ggcaggaaac taaaaaggat tttctccgat tcaagcagaa    60
gttggcctcc aagccggctg tagatgaaag cccagtccac agcctccatg ccccaggccc   120
ggcccgcccc gcgcgcgttt cctgcgccgc agcccggacg tcgagaagat acccttcgct   180
ta                                                                  182
```

<210> SEQ ID NO 23
<211> LENGTH: 131
<212> TYPE: DNA
<213> ORGANISM: Artificial Sequence

```
<220> FEATURE:
<223> OTHER INFORMATION: chemically treated genomic DNA (Homo sapiens)

<400> SEQUENCE: 23
tagggttaga gactcagagc ggagagaggg ggatgggcag ggagagaaga gtggtaatcg      60
cagtgggtct tatactttcc ggatcaagat tagaggctct gctctccgtg ttcacagcgg     120
accttgattt a                                                          131

<210> SEQ ID NO 24
<211> LENGTH: 212
<212> TYPE: DNA
<213> ORGANISM: Artificial Sequence
<220> FEATURE:
<223> OTHER INFORMATION: chemically treated genomic DNA (Homo sapiens)

<400> SEQUENCE: 24
taaacaatcc cgtcaccccc tctcaatgga ccttggggct ctgcgaaata caaggggacc      60
agcctgcctc aaaccctcaa cacctctcgg ccgcagaggc tgtgtcttgg gccagtccct     120
cccgtcccga ctccaacatg gctgctcctt tttaccccag cttatcaagc tgcacatttc     180
cggcagatcc tcccctaaat cagttatttt ta                                   212

<210> SEQ ID NO 25
<211> LENGTH: 167
<212> TYPE: DNA
<213> ORGANISM: Artificial Sequence
<220> FEATURE:
<223> OTHER INFORMATION: chemically treated genomic DNA (Homo sapiens)

<400> SEQUENCE: 25
tacttgatcc gagccccgtg gacccggggt tgccgggatg cctggagtcg ggcgcgcaag      60
actgagcgga gctcttaggg ctgccaggcg tctatggcca taccaccctg aacgcgtcca     120
atctcgtctg atctctcgag gctaagtagg gtcaggcctg gttagta                   167

<210> SEQ ID NO 26
<211> LENGTH: 182
<212> TYPE: DNA
<213> ORGANISM: Artificial Sequence
<220> FEATURE:
<223> OTHER INFORMATION: chemically treated genomic DNA (Homo sapiens)

<400> SEQUENCE: 26
taagaagaat attctggttg ttcgcctgct tggtaaccct gaccctggca gaagaatgag      60
ggaactcatt gcttcaaatt gtcgccaagc ccattaggct acctgaactg tctcagaaag     120
tgcgggtggc tgcgtcgaac ggtggtggct cagaggaaga gattggggcc ggcagcgacc     180
ta                                                                    182

<210> SEQ ID NO 27
<211> LENGTH: 265
<212> TYPE: DNA
<213> ORGANISM: Artificial Sequence
<220> FEATURE:
<223> OTHER INFORMATION: chemically treated genomic DNA (Homo sapiens)

<400> SEQUENCE: 27
tagtggtgga ctcggacgcc gcggacacgg ccagccggcc cggacctcc acggccgcgc       60 tcctggcgca cctgcagcgg cggcgcgagg ctatgcgcgc cgagggcgcc cccgcctcac     120
cgcccagcac cggcacgcgc acctgcacgg tgactgaagg caagcacgcg cgcctcagct     180
```

```
gctacgtgac cggcgagccc aagcccgaga cggtgtggaa gaaggacggc cagctggtga        240
ccgagggccg gcgccacgtg gtgta                                              265

<210> SEQ ID NO 28
<211> LENGTH: 329
<212> TYPE: DNA
<213> ORGANISM: Artificial Sequence
<220> FEATURE:
<223> OTHER INFORMATION: chemically treated genomic DNA (Homo sapiens)

<400> SEQUENCE: 28
tacgaggccg gctgggcggg gggcgctaac gcggctctcg gcgcccccag gggccttcct        60
gctgtgctgg acgcccttct tcgtggtgca catcacgcag gcgctgtgtc ctgcctgctc        120
cgtgcccccg cggctggtca gcgccgtcac ctggctgggc tacgtcaaca gcgccctcaa        180
ccccgtcatc tacactgtct tcaacgccga gttccgcaac gtcttccgca aggccctgcg        240
tgcctgctgc tgagccgggc accccggac gccccccggc ctgatggcca ggcctcaggg        300
accaaggaga tggggagggc gcttttgta                                          329

<210> SEQ ID NO 29
<211> LENGTH: 402
<212> TYPE: DNA
<213> ORGANISM: Artificial Sequence
<220> FEATURE:
<223> OTHER INFORMATION: chemically treated genomic DNA (Homo sapiens)

<400> SEQUENCE: 29
taaagaagaa acagcctctc tccttttcct tattttctaa ttagcatctt acagaggagt        60
ggaaacagct acagcccagt cccctgctca aaactgcgcc accccagttc ggccctgctg        120
ggcgcgcgag ccaaggccgc ggggcaccgg gaggccattt tgcgcgtgcg ctgctcgcct        180
cgcgccgccc tcggctctgc ggactcggat cccgccaaat ttgaacgcga gattgtcagg        240
ccctgagggg cttgagggc gggggaacga cgccgctctc caaagttgga ccccgtggcg        300
agcggcggcg acagccgggt gctcgctgcc tcccgaggtg ctccctttc ccgccgaagc        360 cctccacagc ggcaggccga ggcgcagcga cgtgtccctg ta                          402

<210> SEQ ID NO 30
<211> LENGTH: 219
<212> TYPE: DNA
<213> ORGANISM: Artificial Sequence
<220> FEATURE:
<223> OTHER INFORMATION: chemically treated genomic DNA (Homo sapiens)

<400> SEQUENCE: 30
tagaggtgca aatggccctg ggatccccca ggagcggccc tccaggctct cctctctggc        60
gatcccgagg gcgcgtccgt ccttgggtgt ggaaacccag agggggtcaa ataaatgctc        120
ccctatggaa tttcccactg ctaaggtagt tcggtccagg atgcccgctc aacgcgtatt        180
ggaaggtcag ccgaattgtt gcaatgaaac aaggtttta                               219

<210> SEQ ID NO 31
<211> LENGTH: 179
<212> TYPE: DNA
<213> ORGANISM: Artificial Sequence
<220> FEATURE:
<223> OTHER INFORMATION: chemically treated genomic DNA (Homo sapiens)
```

<400> SEQUENCE: 31

```
taacccttc ctcttttct ttcttatttc cgagaaatct cgcaaacggc gtgaacacta     60
cgctgattcc agaaatggtc gggttccctt ccttcactca ggatggtcgc ctgctgggag   120
ctcatttcga accgagctga acgctcattg ctgagtcctg ggagaaggtc gcgtttgta    179
```

<210> SEQ ID NO 32
<211> LENGTH: 500
<212> TYPE: DNA
<213> ORGANISM: Artificial Sequence
<220> FEATURE:
<223> OTHER INFORMATION: chemically treated genomic DNA (Homo sapiens)

<400> SEQUENCE: 32

```
tacaatgcgg agcggagcac gagggtcgca ggtgcagaac agcgggaaga tgcgctcccc    60 caggggcca ggcgcctgga aggcgtaaag caggtcgagt gagcggccgt cgtagaaggc    120
cacgcggccc cgctcccagt ccaggtccac gcgaatgcgc cgcggcgggg gctcaacacc   180
gcccagcagg gtgggttcgg gtgccgtgag ggcccacagg cggccgccgc ggccctccac   240
ggcccacacg gccccgcag ggcacagcct tacgcagccc ttgcgttgca ctgattcccc    300
ggccgcgccc actgcatagt ggctctcctc gtcgtccgca tcctcccag aagagtctct    360 gcaggaggcg gcgtccgcag tctccacctc ccagcagtgg cggccggccc cgaagccctg   420
cgcacccagc acagctggga gctgattgaa gcgcttgggg ccgtcagggg gcgcgggcgt   480
ccctggtggg gccagttgta                                                500
```

<210> SEQ ID NO 33
<211> LENGTH: 160
<212> TYPE: DNA
<213> ORGANISM: Artificial Sequence
<220> FEATURE:
<223> OTHER INFORMATION: chemically treated genomic DNA (Homo sapiens)

<400> SEQUENCE: 33

```
taacccgtag cataagttag ctcggacata aggcaagccc tcgagaaggg aacgaatcag    60
aaggtgaaaa gagcggtcgg aaggtgagga agagaaggtt taggcgcaac gcctcggagg   120
tattctctga ggccctggcg agatttcggc ctttagctta                         160
```

<210> SEQ ID NO 34
<211> LENGTH: 214
<212> TYPE: DNA
<213> ORGANISM: Artificial Sequence
<220> FEATURE:
<223> OTHER INFORMATION: chemically treated genomic DNA (Homo sapiens)

<400> SEQUENCE: 34

```
taatgagaac gggagcgaac tccacgagtt tgcgcctggg ggagcccagc agcaacccaa    60
gaaaatcagc cttgacatcg aatctccaac gagtggtgac aggcgtccgg accccgtga    120 agaggactga ccggcaccgg atacttctat agcattctcc caacaaacga gatctaacga   180
acccattggc aaggcggtca tccggctgca ctta                               214
```

<210> SEQ ID NO 35
<211> LENGTH: 150
<212> TYPE: DNA
<213> ORGANISM: Artificial Sequence
<220> FEATURE:
<223> OTHER INFORMATION: chemically treated genomic DNA (Homo sapiens)

<400> SEQUENCE: 35

```
taagaacaag tccaacagca ctgctaagca agagcctaat aactcagcgt ttcgcgacat    60
ctcttggcgg cgttgaccgt ttgcccggga cactggttta gaagcacggc atagggtgtc   120
tctacatctt agaaatcaag acagcctcta                                    150
```

<210> SEQ ID NO 36
<211> LENGTH: 463
<212> TYPE: DNA
<213> ORGANISM: Artificial Sequence
<220> FEATURE:
<223> OTHER INFORMATION: chemically treated genomic DNA (Homo sapiens)

<400> SEQUENCE: 36

```
tacagaccat gcacatgaac cactggacgc tggggtatcc caatgtgcac gagatcaccc    60
gctccaccat cacggagatg gcggcggcgc agggcctcgt ggacgcgcgc ttcccttcc   120 cggccctgcc ttttaccacc cacctattcc accccaagca gggggccatt gcccacgtcc   180
tcccagccct gcacaaggac cggccccgtt ttgactttgc caatttggcg gtggctgcca   240
cgcaagagga tccgcctaag atgggagacc tgagcaagct gagcccagga ctgggtagcc   300
ccatctcggg cctcagtaaa ttgactccgg acagaaagcc ctctcgagga aggttgccct   360
ccaaaacgaa aaagagttt atctgcaagt tttgcggcag acactttacc aaatcctaca   420
atttgctcat ccatgagagg acccacacgg acgagaggcc gta                    463
```

<210> SEQ ID NO 37
<211> LENGTH: 130
<212> TYPE: DNA
<213> ORGANISM: Artificial Sequence
<220> FEATURE:
<223> OTHER INFORMATION: chemically treated genomic DNA (Homo sapiens)

<400> SEQUENCE: 37

```
taaggctcaa aaggttctaa acgaagagca tgcggcctga cgcggagcgc aaagaagcga    60
gcagtgaact gaatctggtg ggactgagac cagaggcgtc tgtatgcggc ggccgcttcg   120
cgccctatta                                                          130
```

<210> SEQ ID NO 38
<211> LENGTH: 209
<212> TYPE: DNA
<213> ORGANISM: Artificial Sequence
<220> FEATURE:
<223> OTHER INFORMATION: chemically treated genomic DNA (Homo sapiens)

<400> SEQUENCE: 38

```
tacttgaagg tgcctttgga aagtctgatg aatgagaaat aagtgagcga gtgaatgaat    60
gaataagctg cctaaagcag atgcgtttat gcgtgcattc tctcgagtga aggaagaagg   120
aagaggtagg gacggaggag gagagagagc acgcgcggga aagataaatc gcgcccgccc   180
gcgatggacc ccaatgtcaa tctgatcta                                     209
```

<210> SEQ ID NO 39
<211> LENGTH: 215
<212> TYPE: DNA
<213> ORGANISM: Artificial Sequence
<220> FEATURE:
<223> OTHER INFORMATION: chemically treated genomic DNA (Homo sapiens)

```
<400> SEQUENCE: 39
tacagcacct tcattctgct cttcttcagc ctgtccggcc tcagcatcat ctgcgccatg    60
agtgtcgagc gctacctggc catcaaccat gcctatttct acagccacta cgtggacaag   120
cgattggcgg gcctcacgct ctttgcagtc tatgcgtcca acgtgctctt ttgcgcgctg   180
cccaacatgg gtctcggtag ctcgcggctg cagta                              215

<210> SEQ ID NO 40
<211> LENGTH: 158
<212> TYPE: DNA
<213> ORGANISM: Artificial Sequence
<220> FEATURE:
<223> OTHER INFORMATION: chemically treated genomic DNA (Homo sapiens)

<400> SEQUENCE: 40
taaactccca tggaagtcag gaaatgccgg caaaagcgat ttctggttta cgaagctcgg    60
tttgacgata gcaatttccg ccgaacgcga cttttcctc ttgtggacca agtcgggata   120
tatcagctac tacgattttt tagtcgtaaa caggttta                          158
```

METHOD FOR THE DETERMINATION OF THE DNA METHYLATION LEVEL OF A CPG POSITION IN IDENTICAL CELLS WITHIN A TISSUE SAMPLE

FIELD OF THE INVENTION

The invention relates generally to novel and substantially improved methods for the determination of the DNA methylation level of cells of a subpopulation of cells within a heterogeneous sample.

BACKGROUND OF ASPECTS OF THE INVENTION

Many diseases, in particular cancer diseases, are accompanied by a modified gene expression. This may be a mutation of the genes themselves, which leads to an expression of modified proteins or to an inhibition or over-expression of the proteins or enzymes. A modulation of the expression may however also occur by epigenetic modifications, in particular DNA methylation. Such epigenetic modifications do not affect the actual DNA coding sequence. It has been found that DNA methylation processes have substantial implications for the health, and it seems to be clear that knowledge about methylation processes and modifications of the methyl metabolism and DNA methylation are essential for understanding diseases, for the prophylaxis, diagnosis and therapy of diseases.

The precise control of genes, which represent a small part only of the complete genome of mammals, is a question of the regulation under consideration of the fact that the main part of the DNA in the genome is not coding. The presence of such trunk DNA containing introns, repetitive elements and potentially actively transposable elements, requires effective mechanisms for their durable suppression (silencing). Apparently, the methylation of cytosine by S-adenosylmethionine (SAM) dependent DNA methyltransferases, which form 5-methylcytosine, represents such a mechanism for the modification of DNA-protein interactions. Genes can be transcribed by methylation-free promoters, even when adjacent transcribed or not-transcribed regions are widely methylated. This permits the use and regulation of promoters of functional genes, whereas the trunk DNA including the transposable elements is suppressed. Methylation also takes place for the long-term suppression of X-linked genes and may lead to either a reduction or an increase of the degree of transcription, depending on where the methylation in the transcription unit occurs.

Almost all DNA methylation in mammals is restricted to cytosine-guanosine (CpG) dinucleotide palindrome sequences, which are controlled by DNA methyl transferases. CpG dinucleotides are about 1 to 2% of all dinucleotides and are concentrated in so-called CpG islands. A generally accepted definition of CpG islands is an at least 200 bp long DNA region with a CpG content of at least 50%, and wherein the ratio of the number of observed CG dinucleotides and the number of the expected CG dinucleotides is larger than 0.6 (Gardiner-Garden, M., Frommer, M. (1987) J. Mol. Biol. 196, 261-282; incorporated by reference in its entirety). Typically, CpG islands have at least 4 CG dinucleotides in a sequence having a length of 100 base pairs.

If CpG islands are present in promoter areas, they often have a regulatory function over the expression of the respective gene. In general if the CpG island is hypomethylated, expression can take place. Hypermethylation often leads to the suppression of the expression. In the normal state, a tumor suppressor gene is hypomethylated. If a hypermethylation takes place, this will lead to a suppression of the expression of the tumor suppressor gene, which is frequently observed in cancer tissues. In contrast thereto, oncogenes are hypermethylated in healthy tissue, whereas in cancer tissue they are frequently hypomethylated.

Due to the methylation of cytosine, the binding of proteins regulating the transcription is often prevented. This leads to a modification of the gene expression. With regard to cancer for instance, the expression of cell division regulating genes is often affected, e.g. the expression of apoptosis genes is regulated down, whereas the expression of oncogenes is regulated up. The hypermethylation of the DNA also has a long-term influence on the regulation. By the methylation of cytosine, histone de-acetylation proteins can bind by their 5-methylcytosine-specific domain to the DNA. This has as a consequence that histones are de-acetylated, which will lead to a tighter compacting of the DNA. Thereby, regulatory proteins do not have the possibility anymore to bind to the DNA.

For this reason, the accurate determination of DNA methylation levels is very important. A tailored therapy for the respective person can then be determined. Also the effects of a therapy can be monitored. Moreover the accurate detection of DNA levels is also an important tool for developing new approaches for the prevention, diagnosis and treatment of diseases and for the screening for targets.

Therefore a great technical need exists for highly accurate methods for determining the exact methylation level of cytosines, which are methylated in a disease-specific manner. The present invention makes such a method available. The method according to the invention is more powerful than prior art methods.

An overview for detecting 5-methylcytosine may be gathered from the following review article: Fraga F M, Esteller M, Biotechniques 2002 September, 33(3):632, 634, 636-49 (hereby incorporated by reference in its entirety). The most common methods are based on the use of methylation sensitive restriction enzymes capable of differentiating between methylated and unmethylated DNA and on the treatment with bisulfite.

A method, which is based on the use of methylation sensitive restriction enzymes for determining methylation, is the Differential Methylation Hybridization (DMH, [Huang et al, Hum Mol Genet, 8:459-470, 1999; U.S. patent application Ser. No. 09/497,855] both of these cited references are incorporated by reference to their entirety). According to this method, DNA is initially cut with a single non-methylation-specific restriction enzyme, for instance MseI. The obtained fragments are then ligated with linkers. The thus obtained mixture of fragments is then cut with methylation-specific endonucleases, for instance BstUI and/or HpaII, and amplified by means of linker-mediated PCR. The above steps are performed on the one hand with DNA from a diseased tissue and on the other hand with DNA from adjacent healthy tissue of the same tissue type, and the respectively obtained fragments are labeled with different fluorescence dyes. Both fragment solutions are then co-hybridized on a CpG island microarray. The pattern of fluorescent dots visible therein can then be analyzed to find out, for which CpG clones there are differences in the methylation. As a supplement with regard to the technology and methodological details, reference is made to the documents WO03/087774 and U.S. Pat. No. 6,605,432 (both of these cited references are incorporated by reference to their entirety).

But, in general, the use of methylation sensitive enzymes is limited due to the selectivity of the restriction enzyme towards a specific recognition sequence.

Therefore, the treatment with bisulfite, allowing for the specific reaction of bisulfite with cytosine, which, upon subsequent alkaline hydrolysis, is converted to uracil, whereas 5-methylcytosine remains unmodified under these conditions (Shapiro et al. (1970) Nature 227: 1047; hereby incorporated by reference in its entirety)) is currently the most frequently used method for analyzing DNA for 5-methylcytosine. Uracil corresponds to thymine in its base pairing behavior, that is it hybridizes to adenine; whereas 5-methylcytosine does not change its chemical properties under this treatment and therefore still has the base pairing behavior of a cytosine, that is hybridizing with guanine. Consequently, the original DNA is converted in such a manner that 5-methylcytosine, which originally could not be distinguished from cytosine by its hybridization behavior, can now be detected as the only remaining cytosine using "normal" molecular biological techniques, for example, amplification and hybridization or sequencing. All of these techniques are based on base pairing, which can now be fully exploited.

In patent application WO05/038051 (hereby incorporated by reference in its entirety) improvements for the conversion of unmethylated cytosine to uracil by treatment with a bisulfite reagent are described. According to this method the reaction is carried out in the presence of a aliphatic cyclic ether (e.g. dioxane) or in the presence of a n-alkylene glycol compound (e.g. diethylene glycol dimethyl ether). The bisulfite conversion is conducted at a temperature in the range of 0-80° C. with 2 to 5 thermos-pikes (brief incubation at increased temperature of 85-100° C.).

Subsequent to a bisulfite treatment, usually short, specific fragments of a known gene are amplified and either completely sequenced (Olek A, Walter J. (1997) The pre-implantation ontogeny of the H19 methylation imprint. Nat. Genet. 3: 275-6; hereby incorporated by reference in its entirety) or individual cytosine positions are detected by a primer extension reaction (Gonzalgo M L and Jones P A. (1997) Rapid quantitation of methylation differences at specific sites using methylation-sensitive single nucleotide primer extension (Ms-SNuPE). Nucleic Acids Res. 25: 2529-31, WO 95/00669; both of these cited references are incorporated by reference in its entirety) or by enzymatic digestion (Xiong Z, Laird P W. (1997) COBRA: a sensitive and quantitative DNA methylation assay. Nucleic Acids Res. 25: 2535-4; hereby incorporated by reference in its entirety).

Another technique to detect the methylation status is the so-called methylation specific PCR (MSP) (Herman J G, Graff J R, Myohanen S, Nelkin B D and Baylin S B. (1996), Methylation-specific PCR: a novel PCR assay for methylation status of CpG islands. Proc Natl Acad Sci USA. 93: 9821-6; hereby incorporated by reference in its entirety). The technique is based on the use of primers that differentiate between a methylated and a non-methylated sequence applied after bisulfite treatment of said DNA sequence. The primer either contains a guanine at the position corresponding to the cytosine in which case it will after bisulfite treatment only bind if the position was methylated. Alternatively the primer contains an adenine at the corresponding cytosine position and therefore only binds to said DNA sequence after bisulfite treatment if the cytosine was unmethylated and has hence been altered by the bisulfite treatment so that it hybridizes to adenine. With the use of these primers, amplicons can be produced specifically depending on the methylation status of a certain cytosine and will as such indicate its methylation state.

A further technique is the detection of methylation via a labelled probe, such as used in the so-called Taqman PCR, also known as MethyLight™ (U.S. Pat. No. 6,331,393; hereby incorporated by reference in its entirety). With this technique it became feasible to determine the methylation state of single or of several positions directly during PCR, without having to analyze the PCR products in an additional step.

In addition, detection by hybridization has also been described (Olek et al., WO 99/28498; both of these cited references are incorporated by reference to their entirety).

The quantification of methylation, e.g. a quantitative detection of the DNA methylation level or the amount of methylated or unmethylated DNA, is possible according to the state of the art by several methods (Laird, P. Nat Rev Cancer 2003; 3(4):253-66.; hereby incorporated by reference in its entirety). These methods are usually based on bisulfite treatment and subsequent amplification. In most cases the analysis takes place after the amplification (e.g. Ms-SNuPE, hybridisation on microarrays, hybridisation in solution or direct bisulfite sequencing; for review: Fraga and Esteller 2002, loc. cit.; hereby incorporated by reference in its entirety). However, this "endpoint analysis" leads to several problems; e.g. product inhibition, enzyme instability and decrease of the reaction components, with the result that the amplification does not proceed uniformly. Therefore a correlation between the amount of input DNA and the amount of amplificate does not always exist. As a consequence, the quantification is error-prone (for review: Kains: The PCR plateau phase—towards an understanding of its limitations. Biochem. Biophys. Acta 1494 (2000) 23-27; hereby incorporated by reference in its entirety).

The real time PCR based MethyLight™ technology uses a different approach for a quantification (for review U.S. Pat. No. 6,331,393; hereby incorporated by reference in its entirety). In brief, this method analyses the exponential phase of the amplification instead of the endpoint. Traditionally a threshold cycle number (Ct) is calculated from the fluorescence signal that describes the exponential growth of the amplification (P S Bernard and C T Wittwer, Real-time PCR technology for cancer diagnostics, Clinical Chemistry 48, 2002; hereby incorporated by reference in its entirety). The Ct value is dependent on the starting amount of methylated DNA. By comparing the Ct value of an experimental sample with the Ct value of a standard curve the methylated DNA can be quantified (for review: Trinh et al. 2001, loc. cit.; Lehmann et al.: Quantitative assessment of promoter hypermethylation during breast cancer development. Am J Pathol. 2002 February; 160(2):605-12; both of these cited references are incorporated by reference to their entirety).

There are two commonly used methods to calculate the Ct value. The threshold method selects the cycle when the fluorescence signal exceeds the background fluorescence. The second derivative maximum method selects the cycle when the second derivative of the amplification curve has its maximum. For classical real-time PCR assays both methods produce identical results.

However, both methods do not produce exact results for the quantification of methylation via MethyLight™ assays. The MethyLight™ technology normally uses a methylation specific amplification (by methylation specific primers or blockers, sometimes methylation unspecific primers are used) combined with a methylation specific probe (for review: Trinh et al., 2001, loc. cit.; hereby incorporated by reference in its entirety). The methylation specific probe results in fluorescence signals from only a part of the generated amplificates depending on the methylation status of the CpG positions covered by the probe. This results in amplification curves that are downscaled compared to curves from completely methylated template DNA. These downscaled curves are the reason that both analysis methods generate incorrect results.

The threshold method assumes that all curves are in their exponential growth phase when exceeding the threshold. However, for samples with low proportions of DNA that is methylated at the probe (especially common in cancer diagnostics) this is not true. Amplification curves are already in the plateau phase and Ct estimation will be wrong.

The second derivative maximum method is independent from the overall intensity of the amplification curve. It only takes the shape into account which corresponds to a quantification of DNA that is methylated at the priming sites. The information generated by the methylation specific probe—represented by the signal intensity—is not used.

An improved method is the MethyLight™ ALGO™ method (EP 04090255.3; hereby incorporated by reference in its entirety), which is based on the MethyLight™ technology. According to this improved method, the degree of methylation is calculated from the signal intensities of probes using different algorithms.

A further method is the so-called QM™ assay (for review PCT/EP2005/003793, hereby incorporated by reference in its entirety), which is also based on real-time PCR. According to this method, a non-methylation-specific, conversion-specific amplification of the target DNA is produced. The amplificates are detected by means of the hybridization of two different methylation-specific real-time PCR probes. One of the probes is specific for the methylated state, while the other probe is specific for the unmethylated state. The two probes are labelled with different fluorescent dyes. The quantification of the degree of methylation can be carried out during specific PCR cycles by employing the ratio of signal intensities of the two probes. Alternatively, the Ct values of two fluorescent channels can also be drawn on for the quantification of the methylation. In both cases, quantification of the degree of methylation is possible without the necessity of determining the absolute DNA quantity. A simultaneous amplification of a reference gene or a determination of PMR values is thus not necessary. In addition, the method supplies reliable values for both large and small DNA quantities as well as for high and low degrees of methylation.

The third preferred method for quantitative detection of DNA methylation is the so-called restriction assay, also known as Mest evaluation (PCT/DE205/001109; hereby incorporated by reference in its entirety). In brief, according to this method, DNA is digested with at least one methylation-specific restriction enzyme. After this, the digested DNA is subjected to real time PCR amplification. But amplificates are only amplified from said DNA if the DNA was not previously cut by the methylation-specific enzyme or enzymes within the sequence of the amplificate. The percentage of methylated DNA is then deduced by comparison of the signal intensity obtained for the sequence of interest with that of a reference sample.

According to the said methods, a quantification of methylation levels is possible. But recent studies have shown, that they only have a limited accuracy making a precise characterization of samples very difficult. Therefore the differentiation, grading, and staging of diseased tissue is impaired and therefore also the diagnosis of proliferative disorders or predisposition to those.

Because of that, it is the technical object of the invention to provide a quantitative method for DNA methylation analysis which has a higher accuracy than the known methods. Consequently, a liable differentiation, grading, and staging of diseased tissue and therefore also the diagnosis of proliferative disorders or predisposition to those is enabled.

Very surprisingly, this technical need can be fulfilled by a simple approach according to the invention. The present invention addresses the problem, heretofore unrecognized, that the majority of biological samples isolated from a patient are a heterogenous mixture of a plurality of pathologically cell types e.g. healthy tissue and diseased tissue. The method of the invention enables the quantification of selected tissue or cellular type(s) within said heterogenous biological sample. Said method is particularly useful in the field of pathology wherein a biological sample from a patient is often a heterogeneous mixture of healthy and sick cells. By enabling the quantification of the amount of healthy and sick cells within a sample the invention assists in the quantification of disease markers within said sample.

DETAILED DESCRIPTION OF ASPECTS OF THE INVENTION

Figure 1:
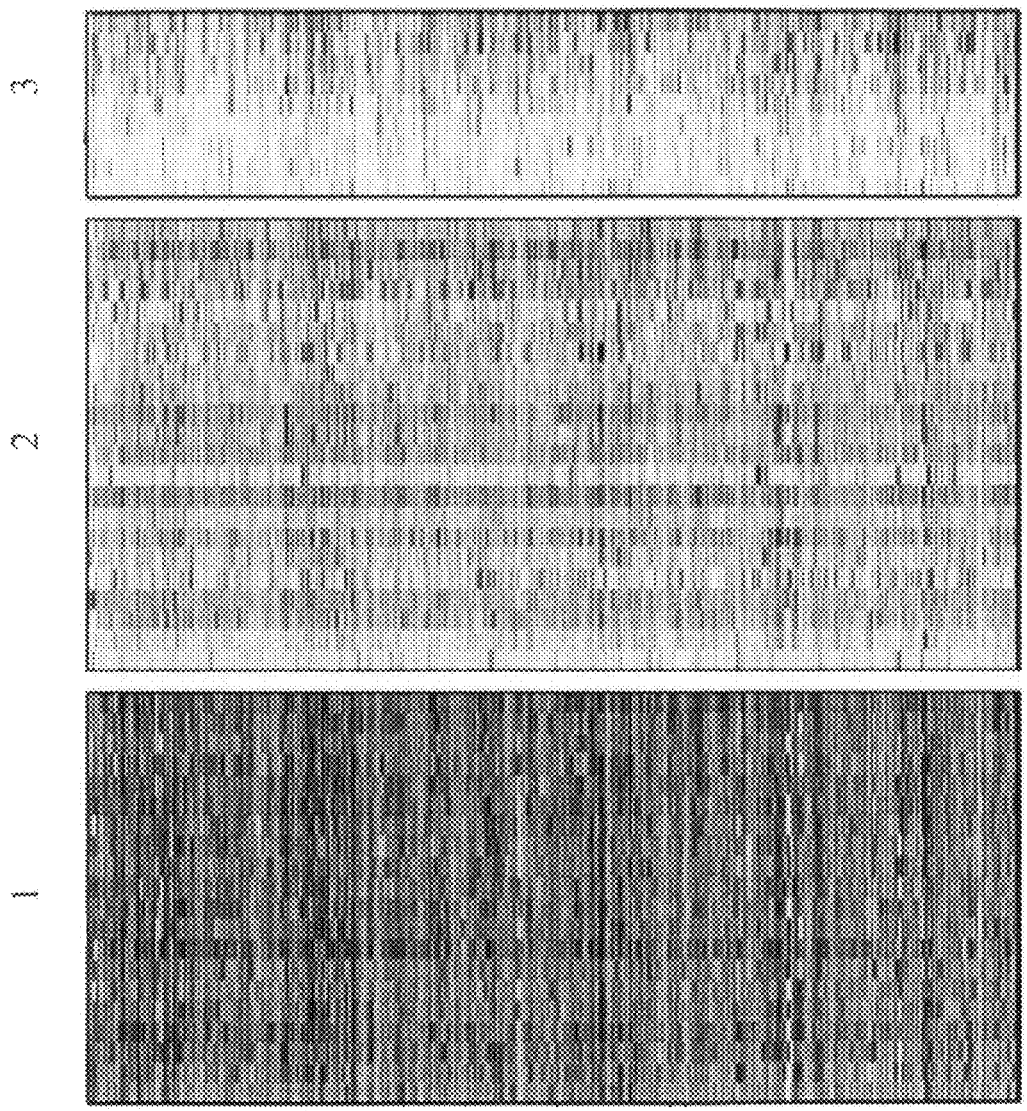
FIGS. 1 and 2 each provide a matrix of the quantified methylation value of genomic CpG positions as measured by means of DMH according to Example 1. Each row of a matrix represents a DMH fragment and each column represents an individual DNA sample. The degree of methylation represented by the shade of each position within the column from black representing 100% methylation to light grey representing 0% methylation. 'A' indicates normal tissue, 'B' indicates surgically removed lung cancer samples and 'C' indicates lung cancer cell lines.

For achieving the technical object, the invention teaches a method for the determination of the DNA methylation level of one or more specific CpG positions of a subpopulation of cells within a tissue sample. The method comprises a) the determination of the cell content of a subpopulation of cells within the sample, b) the measurement of the total DNA methylation level of said one or more specific CpG positions within the tissue sample, c) determination of the DNA methylation level within cells of said subpopulation of cells form the total DNA methylation level of said one or more specific CpG positions within the tissue sample and the cell content of said subpopulation of cells within the tissue sample.

The central idea of the present invention is to consider samples taken from tumor tissue no longer as homogeneous as it is done according to methods of the state of the art.

Instead, according to the invention, only cells which really contributed to the state of interest of the diseased tissue are taken into account. Other cells always also part of the tumor are excluded from analysis. Of course, this central idea is not limited to tumor tissue, it can be also transferred to any quantitative analysis of DNA methylation, wherein the sample to be analysed might be hetereogeneous.

ADVANTAGES OF THE INVENTION

The method of the invention has the following advantages: It has a higher specifity, a higher reliability and a higher reproducibility than the sofar known methods according to the state of the art.

The reason for this is that the methods of the state of the art consider a sample taken from a tumor as homogeneous. According to them, every cell within a sample is thought to comprise the same tumor specific changes in DNA methylation.

However, the amount of cells which are really specific for the tumor, its stage, grade, or differentiation is varying depending on numerous factors such as the tumor type, or the stage, grade, differentiation and origin of the tumor. According to the invention only cells of a single type are taken into consideration which really contribute to the state of interest of the diseased tissue. This leads to an improved accuracy because the method of the invention is based on the known methods for DNA methylation analysis. The higher accuracy is thereby accompanied by a improved reliablity and an improved reproducibility.

Moreover, the higher accuracy has the additional advantage that tumors can even be analysed which comprise only a small number of altered cells distributed over a large area, for example liposarcoma, adeno carcinoma or Morbus Hodkin. This has sofar not or only to a limited extent been possible with the known methods of the state of the art.

Of course, the method of the invention can in general be addressed to other problems, in which the DNA methylation of at least two different subpopulation of cells is mixed to various degrees.

EMBODIMENTS OF THE INVENTION

A preferred embodiment of the invention is a method for the determination of the DNA methylation level of one or more specific CpG positions of a subpopulation of cells within a tissue sample, comprising
a) a determination of the cell content of said subpopulation of cells within the tissue sample in a quantitative or semiquantitative manner,
b) measuring the total DNA methylation level of said one or more specific CpG positions within the tissue sample, and
c) determining the DNA methylation level within the cells of said subpopulation of cells from the total DNA methylation level of said one or more specific CpG positions within the tissue sample and the cell content of said subpopulation of cells within the tissue sample.

The term "methylation level" represents hereby the quantitatively determined, average occupancy of methylcytosine at a single CpG dinucleotide in the genome across an entirety of DNA molecules (Siegmund, K D, Laird, P W. Methods 2002; 27(2):170-8.; hereby incorporated by reference in its entirety). According to the invention, it is possible to determine more than one different methylation levels simultaneously. The entirety of DNA molecules is hereby defined in that it is derived from the genome of cells which belong all to the same type of cells herein referred as single cell type.

The tissue sample can be any kind of sample derived from a human being. Preferably the tissue sample is a biopsy or surgical sample derived from a tissue. It can also be preferably a remote sample such as sputum, stool or any bodily fluid, in particular serum, plasma, whole blood, saliva, urine, fluids from the pleural or peritoneal cavity, cerebrospinal fluid or a smear from a epithelial surface. Of course, also samples which are enriched with regard to a certain type or types of cells are also preferably used for the method according to the invention. In general, the sample can be treated in different ways for use in the method of the invention. For example fresh, fresh frozen or archived samples such as paraffin-embedded and/or formalin-fixed samples are useable. Of course, samples treated differentially are also useable as long as the enable at least one of the embodiments of the invention for determining the cell content of a subpopulation of cells or the DNA methylation analysis.

According to a preferred embodiment of the invention, the content of cells of a subpopulation of cells is determined by means of staining methods, in particular by means of standard histotechnologic methods. Numerous suitable methods are well known to those with ordinary skills in the art. A rough overview could be gained from the following literature: Burck, H C. Histologische Technik: Leitfaden für die Herstellung mikroskopischer Präparate in Unterricht und Praxis. 6. edition, Thieme, 2002; Kiernan, J A. Histological and histochemical methods: theory and practice. 2. edition, Arnold Publishers, 1990; Ackermann and Rosai (editors). Surgical pathology. 9. edition, Mosby, 2004; Killeen, A A. Principles of Molecular Pathology. Humana Press, 2003; Romeis, B. Mikroskopische Technik. R. Oldenbourg Verlag, 1968 (all of these cited references are incorporated by reference to their entirety). But many more staining methods are known in the art and may be used according to the invention.

In a preferred embodiment, the cell content of a subpopulation of cells is determined by means of the following stainings:

Hematoxilin/Eosin stain, a universal staining method for the demonstration of nuclear features (stained by Hematoxilin in blue) and cytoplasm (stained by Eosin in red).

Papadopulos stain, a standard staining used in cervical cytology. It allows best to differentiate squamous cells from different layers of the portio and their transformations.

Histochemical protocols that allow the specific labeling of tissues components. Numerous of such methods are known to those with ordinary skills in the art. Exemplary, only the Giemsa Stain (nuclear features), the Elastica-van Gieson Stain (connective tissue), the Ladewig Stain (connective tissue), and the Tri PAS Stain (mucus) are listed here.

Further suitable stainings are

Perjodic Schiff Acid (PAS) Stain, which demonstrates glycogen and neutral mucosubstances. It further outlines basement membranes and is useful for the demonstration of the intracytoplasmic crystals in alveolar soft part sarcoma.

Argentaffin and argyrophilic stains. The staining with argentaffin depends on the presence of a substance in the tissue. Many times, such a substance comprises a phenolic group that reduces silver and other metallic salts. Examples for said substance are catecholamines or indolamines. A popular protocol for an argentaffin/argyrophilic stain is the staining of paraffin sections according to the Fontana-Masson stain. In general, silver stains are mainly used for the identification of neuroendocrine cells and their tumors. But they can also be used for the demonstration of reticulin fibers, melanin and calcium.

Amyloid stains, of which numerous methods are know to those skilled in the art. Exemplary, only the Congo Red Stain is mentioned. This staining allows the examination with standard as well as polarized light. It is regarded as the most reliable and practical technique to detect amyloid.

Reticulin stains, which demonstrate both reticular fibers and basement membrane material. Reticular fibers consist of very thin fibers of mainly type II collagen, which are widespread in connective tissue throughout the body. Basement membranes are largely composed of type IV collagen and laminin. Numerous reticulin stains are known in the art. Examplary reticulin stains, in particular the Gomori's Stain, the Wilder's Stain, the Gordon Stain, and the Sweets Stain are mentioned. Preferably this stains are used in tumor pathology to distingiush the following: i) epithelial from non epithelia neoplasms, ii) various mesenchymal neoplasms from each other, and iii) in situ from invasive carcinoma.

Further stains are for example staining methods for hemosiderin, such as the Perls Stain, or for calcium, such as the von Kossa Stain. According to the Perl's Stain, hydrochloric acid splits off the protein bound to the iron allowing the potassium ferrocyanide to combine specifically with the ferric ion to form ferric ferrocyanide also known as Prussion blue. In the von Kossa staining method, calcium is substituted by silver in calcium salts. The silver salt is then reduced to black metalic silver by the use of light or a photographic developer.

Other staining methods stain for example neutral lipids. Preferably, this staining is used for the distinction between fibroma and thekoma in the ovary. It further preferably used for the diagnosis of renal cell carcinoma and sebaceous gland tumors of the skin.

As already said, numerous staining methods are well known to those skilled in the art. Of course, also so far unknown methods may be used according to the invention as long as they allow a determination of cells of a subpopulation of cells.

In a preferred embodiment, the content of cells of a subpopulation of cells is determined by means of staining methods which are based on specific antibodies. Numerous suitable methods are well known to those with ordinary skills in the art. A rough overview could be gained from the following literature: Burck, H C. Histologische Technik: Leitfaden für die Herstellung mikroskopischer Präparate in Unterricht und Praxis. 6. edition, Thieme, 2002; Kiernan, J A. Histological and histochemical methods: theory and practice. 2. edition, Arnold Publishers, 1990; Ackermann, Rosai (editors). Surgical pathology. 9. edition, Mosby, 2004; Killeen, A A. Principles of Molecular Pathology. Humana Press, 2003; Romeis, B. Mikroskopische Technik. R. Oldenbourg Verlag, 1968 (all of these cited references are incorporated by reference to their entirety). But many more staining methods are known in the art and may be used according to the invention. Of course, also so far unknown methods based on specific antibodies may be used according to the invention as long as they allow a determination of cells of a subpopulation of cells.

In a preferred embodiment, the cell content of a subpopulation of cells is determined by means of antibody based stainings. The antibodies are used for the specific detection of antigens. They are either monoclonal antibodies or polyclonal antibodies. Furthermore they are produced in different animals: for example monoclonal antibodies in mouse and polyclonal antibodies in rabbit, donkey, sheep or chicken. The detection of the specifically bound antibody to an antigen may be achieved by direct labeling of the antibody e.g. with a fluorescent dye. But also, and more commonly used, labeled bridging antibodies are used, which specifically bind to the constant region of the primary antibody. In preferred embodiments, the antibodies for detection are linked to fluorescent dyes which allow a specific detection by means of a fluorescence microscope. Numerous of such fluorescent dyes are known to those with ordinary skills in the art. In particular preferred are Cy2, Cy3 and/or Cy5. An overview of other suitable fluorescent dyes can be obtained from the "Fluorochrome Wall Chart" published by Zeiss (Germany; 45-0033; hereby incorporated by reference in its entirety).

In another preferred embodiment, the antibodies for detection are modified by linkage to additional enzymes, proteins, peptides or chemical substances which are allow the detection. These molecules enable a detection of a specific antibody binding to an antigen by means of a light microscope. In a particular preferred embodiment, the detection may comprise the use of one or more of the following: biotin, avidin, horse reddish peroxidase, diaminobendzidin, and/or Envision. Numerous kits are available for the detection of antigen by means of light microscopy. Companies who provide such kind of kits are for example DAKO (Glostrup, D K) or Vector Labs (Burlingame, Calif., USA). But, of course other kits may also be used according to the invention.

According to the invention, any antibody can be used, specific for any antigen, as long as it can be used for the determination of a subpopulation of cells.

A preferred embodiment is characterized in that the cell content of said subpopulation of cells is determined by using staining methods or specific antibodies.

In a preferred embodiment, the cells of said subpopulation of cells are disease-associated cells. In particular these cells might be tumor-associated cells. Numerous methods are known to those with ordinary skills in the art to identify a tumor-associated cell in a tissue sample. For an rough overview please refer to Ackermann, Rosai (editors). Surgical pathology. 9. edition, Mosby, 2004 and to Killeen, A A. Principles of Molecular Pathology. Humana Press, 2003; hereby incorporated by reference in its entirety). Exemplary, tumor-associated cell may be identified according to the following criteria:

Cytologic or cytomophologic criteria of malignancy may be
a) polymorphism e.g. differences in the aspect of individual cells in a tumor, up to giant nuclei that have the size of several normal nuclei;
b) nuclear hyperchromasia e.g. increased nuclear uptake of Hematoxilin;
c) an increased ration of nucleus to cytoplasm, interpreted as a sign of increased nuclear metabolic activity;
d) prominent nucleolus, interpreted as a sign of increase nuclear synthesis activity; or
e) other cell morphologies or features, that are typically described for the individual tumor, and often named after the first describer. A person with ordinary skills in the art knows these morphologies or features for example, but not limited to the Reed-Sternberg cells in Morbus Hodgkin, the Hodgkin cells in Morbus Hodgkin, the signet ring cell in gastric carcinoma, the lipoblasts in liposarcoma, the cristalloids in prostate carcinoma. Furthermore, so far unknown cell morphologies or features are also preferred which will be discovered to be linked to disease-associated cells.

With regard to histologic criteria the main criteria of malignancy of cells is infiltrative growth. This may vary depending on the tumor. Infiltration in epithelial tumor cells is often defined as growth beyond the basal lamina. Tissues that show the cytologic criteria of malignancy but do not penetrate the basal lamina are called dysplasia. They are pre-neoplasias and have a high risk to become invasive, but they do not yet infiltrate and metastasize. An example is the cervical intraepithelial neoplasia (CIN) a precessor of the squamous carcinoma of the cervix. Similar changes may be found in the larynx and the skin. In contrast, urothelial papillary neoplasms are called carciomas also when they do not infiltrate beyond the basal lamina. Another criteria is the presence of desmoplastic stroma. For example, colonic adenomas, precessors of colon carcinoma, do not display demoplastic stroma. However, infiltrative carcinomas, having developed within an adenoma, display fibroblastic proliferations (desmoplastic stroma) around their glandules. In some lymphomas (e.g. MALT B cell lymphoma) malignancy may be signified by the presence of lymphoid cells within the mucosa so-called lymphoepithelial lesions. Of course, the said are only examples to which the subject matter of the invention is not limited.

Moreover malignant tumor cells may grow either in solid, glandular, cribriform, or single cell pattern, sometimes displaying also special patterns. These patterns are well known to those skilled in the art, for example, but not limited to Homer-Wright-Rosettes in malignant periphery nerve sheath tumors or in undifferentiated neuroblastomas, or Schiller-Duval bodies in yolk-sack tumors, or Indian file pattern. Furthermore, significant cell morphologic changes over the area of the tumor as well as in the recurring tumor in comparison to the primary tumor are observeable.

A further histological citeria for malignancy of cells are blood and lymphatic vessel infiltration or growth beyond the tumor capsule for example in follicular carcinoma of the thyroid gland.

In another preferred embodiment, disease-associated cells are specifically detected by means of antigens associated with these cells. Suitable antigens or the corresponding antibodies for specific detection are well known to those with ordinary skills in the art, for example, but not limited to pan cytokeratin antibodies such as AE1/AE3 (DAKO, Glosrup, DK)), antibodies useful for the determination of proliferation rates such as MIB 1 antibodies (DAKO, Glosrup, DK), or antibodies which detect specific immunhistochemical markers. Antibodies of this purpose may be directed against cytoskeleton proteins, hormones, antigens of the lymphoreticular or hematopoetic system, oncofetal antigens, proteinase inhibitors, viral and neural antigens, tissues and cell specific antigens, blood group antigens, or oncogene products. Of course, antibodies specific for other antigens even if they are so far unknown can be used according to the invention as long as the are useful for detecting disease-associated cells.

A preferred embodiment is characterized in that the cell content of said subpopulation of cells is determined by histopathology.

In a preferred embodiment, the identified cells of said subpopulation of cells, in particular the identified disease-associated cells, are counted and the corresponding cell content is determined with reference to the total amount of cells in a given area.

In a further preferred embodiment, the above said antibodies may be used for automatized cell counting. Several methods are known to those skilled in the art. Such methods are for example, but not limiting to a method essentially carried out according to Demirkaya, O. et al. Anal Quant Cytol Histol. 1999 April; 21(2):93-102.; to Coon, J S. Lab Invest. 1987; 57(5):453-79; to Sjöström, P J. et al. Cytometry. 1999, 36(1): 18-26; or to Xu, Y H. et al. Comput Methods Programs Biomed. 2000; 63(1):55-70 (all of these cited references are incorporated by reference to their entirety). According to these methods, cells of the subpopulation of cells of interest are labeled immunhistochemically with one or more antibodies and compared to all nuclei. The nuclear stain may be performed with DAPI (fluorescence detection) or with Hematoxilin (detection by means of light microscopy). But also other suitable nuclear stains are known to those skilled in the art and therefore included herewith. Of course other so far unknown nuclear stains may be used according to the invention.

In another preferred embodiment, the FACS analysis is used. This technique has the advantage that the cell content of a subpopulation of cells of interest is directly determined with high accuracy. Various suitable methods are known those with ordinary skills in the art. In brief, the tissue sample has to be lysed to allow the preparation of a cell suspension of single cells. The single cells are then labeled subpopulation specifically with corresponding antibodies. Thereafter the labeled cells are sorted and counted. The cell content of the subpopulation of cells of interest is then determined by the ratio of the amount of cells of the subpopulation of cells of interest to the amount of the total cells.

In a preferred embodiment, the content of cells of a subpopulation of cells is determined by using expression analysis. Such an analysis can be any analysis method which determines quantitative or semiquantitative the amount of one or more proteins, peptides, RNAs or other chemical compounds which are specific for the said subpopulation of cells. Chemical compounds may be for example hormones or metabolic compounds. In principle, analysis methods may be used as already known to those skilled in the art, as well as sofar unknown methods. In particular, analysis methods are preferred which are based on Western Blot analysis, Northern Blot analysis, Southern Blot analysis, ELISA, PCR, or DNA arrays. A person with ordinary skills in the art will know to choose an appropriate analysis method for expression analysis which is suitable for determination of the cell content of a subpopulation of cells of interest.

In a preferred embodiment of the invention the cells of said subpopulation of cells are disease-associated cells. Such kind of cells may be detected by the detection of special chromosomal aberrations within cells. This aberrations may be for example, but not limited to break-points, deletions, polysomias, or gene amplifications. They can be detected for example by means of PCR, Southern Hybridisation, in situ hybridisation, FISH analysis or CGH analysis. These methods are well known to those skilled in the art. Also oncogenic viruses like HPV or EBV may also be detected by means of FISH analysis or PCR.

A preferred embodiment of the invention is characterized in that the cell content of said subpopulation of cells is determined by using expression analysis.

In another preferred embodiment, the content of cells of a subpopulation of cells is determined by DNA methylation analysis. Thereby the methylation of one or more markers specific for one or more subpopulations of cells is analysed. Such a marker may comprise one or more CpG positions. In the simplest case the subpopulation of cells specific marker is a locus which comprises only a single CpG position. The DNA methylation at this single CpG position is then determined quantitatively as already described in detail above. On the other side, the subpopulation of cells specific marker may comprise more than one CpG position. If it is specific for the subpopulation of cells of interest that all CpG positions are methylated or unmethylated simultaneously, then it is sufficient to determine only the methylation of a single CpG position of the subpopulation of cells specific marker in a quantitative manner. Of course, it is also possible, and also preferred in other embodiments, to determine the DNA methylation quantitatively of a subset of CpG positions or of all CpG positions of the subpopulation of cells specific marker. In all three cases, the quantitative methylation is also determined as described above. However, in other embodiments more than one CpG position is comprised within the subpopulation of cells specific marker and the different CpG positions are methylated differentially. In this case, the methylation pattern of these CpG positions is determined which is specific for the subpopulation of cells of interest in a quantitative manner. For this, several suitable methods are known to those skilled in the art. Preferably, bisulfite sequencing directly or after cloning of the DNA fragments, or primer extension are used.

In a preferred embodiment of the invention the determined methylation of one or more subpopulation of cells specific markers is compared to values obtained from reference samples. The reference samples comprise cells of said subpopulation of cells and have a known cell content of said cells.

A preferred embodiment of the invention is characterized in that the cell content of said subpopulation of cells is determined by DNA analysis.

In a particular preferred embodiment the cell content of a subpopulation of cells of interest is determined from the total DNA amount and the amount of DNA which is methylated at one or more CpG positions of a defined locus. The methylation of said locus is thereby specific for said subpopulation of cells. Of course it is also possibly to consider more than one locus. In this case the results for the amount of methylated DNA and for the total DNA amount are each averaged. The ratio of the amount of methylated DNA to the total DNA amount represents then the cell content of the subpopulation of cells of interest in the sample.

In other particular preferred embodiments, it is specific for said subpopulation of cells that one or more cytosines at a defined locus are unmethylated. Also in this case it is possible to consider more than one locus. For this, the results for the amount of unmethylated DNA and for the total DNA amount are each averaged. The cell content of said subpopulation of cells is then represented by the ratio of the difference between the total DNA amount and the amount of unmethylated DNA to the total DNA amount.

A preferred embodiment is characterized in that the cell content of said subpopulation of cells is determined by
a) measuring, in one or more loci, the total DNA amount present in the tissue sample,
b) measuring, in one or more loci, the amount of methylated DNA,
c) determining the cell content of said subpopulation of cells in the tissue sample, as the amount of methylated DNA within the total DNA.

In particular preferred embodiment, the cell content of a subpopulation of cells of interest in determined from the total DNA amount and the amount of unmethylated DNA. Thereby it is specific for said subpopulation of cells that one or more cytosines at a defined locus are unmethylated. Of course it is also possibly to consider more than one locus. In this case the results for the amount of unmethylated DNA and for the total DNA amount are each averaged. The ratio of the amount of unmethylated DNA to the total DNA amount represents then the cell content of the subpopulation of cells of interest in the sample.

In another particular preferred embodiment, the methylation of said locus is specific for said subpopulation of cells. The cell content of said subpopulation of cells is then represented by the ratio of the difference between the total DNA amount and the amount of unmethylated DNA to the total DNA amount. Also in this case it is possible to consider more than one locus. For this, the results for unmethylated DNA and for the total DNA amount are each averaged.

The total DNA amount of the above said embodiments is determined according to standard techniques. Numerous methods are known to those skilled in the art. But also other, sofar unknown methods are usable, which enable the determination of the amount of DNA.

A preferred embodiment of the invention is characterized in that the cell content of said subpopulation of cells is determined by
a) measuring, in one or more loci, the total DNA amount present in the tissue sample,
b) measuring, in one or more loci, the amount of unmethylated DNA,
c) determining the cell content of said subpopulation of cells in the tissue sample, as the amount of unmethylated DNA within the total DNA.

In particular preferred embodiment, the cell content of a subpopulation of cells of interest in determined from the amount of unmethylated DNA and the amount of methylated DNA. Thereby it is specific for said subpopulation of cells that one or more cytosines at a defined locus are methylated. Of course it is also possibly to consider more than one locus. In this case the results for the amount of unmethylated DNA and for the total DNA amount are each averaged. The ratio of the amount of methylated DNA to the sum of the amount of unmethylated DNA and the amount of methylated DNA represents then the cell content of the subpopulation of cells of interest in the sample.

In another particular preferred embodiment, it is specific for said subpopulation of cells that one or more cytosines at a defined locus are unmethylated. Also in this case it is possible to consider more than one locus. For this, the results for the amount of unmethylated DNA and the amount for methylated DNA are each averaged. The cell content of said subpopulation of cells is then represented by the ratio of the amount of unmethylated DNA to the sum of the amount of unmethylated DNA and the amount of methylated DNA.

A preferred embodiment of the invention is characterized in that the cell content of said subpopulation of cells is determined by
a) measuring, in one or more loci, the unmethylated DNA amount present in the tissue sample,
b) measuring, in one or more of said loci, the methylated DNA amount present in the tissue sample,
c) determining the cell content of said subpopulation of cells of the tissue sample as the ratio of methylated DNA to unmethylated plus methylated DNA, or as the ratio of unmethylated DNA to unmethylated plus methylated DNA.

According to a further preferred embodiment, the ratio of the amount of methylated to the amount of unmethylated DNA is used for deducing the cell content of the subpopulation of cells of interest. This is in particular preferred in cases in which it is favourable for technical reasons to measure the ratio of methylated to unmethylated DNA or the ratio of unmethylated to methylated DNA. A person with ordinary skill in the art knows numerous possibilities how to deduce the cell content from said ratios. For example, the cell content can be deduced by equating the amount of methylated DNA to the ratio of methylated to unmethylated DNA and equating the amount of unmethylated DNA to 1. With these equations it is possible to obtain the cell content according to the above explained embodiments. On the other hand, it is also possible to deduce the cell content according to the above explained embodiments by equating the amount of unmethylated DNA to the ratio of unmethylated to methylated DNA and equating the amount of methylated DNA to 1. Further possibilities for deducing the cell content of a tissue sample are: i) comparing the ratio of methylated to unmethylated DNA of the tissue sample with the ratio of methylated to unmethylated DNA of a reference sample with known cell content; or ii) comparing the ratio of unmethylated to methylated DNA of the tissue sample with the ratio of unmethylated to methylated DNA of a reference sample with known cell content.

A further preferred embodiment of the invention is characterized in that the cell content of said subpopulation of cells is determined by
a) measuring, in one or more loci, the ratio of methylated DNA to unmethylated DNA present in the tissue sample, or by measuring, in one or more loci, the ratio of unmethylated DNA to methylated DNA present in the tissue sample, and
b) determining the cell content of said subpopulation of cells of the tissue sample from the ratio of methylated DNA to unmethylated DNA, or from the ratio of unmethylated DNA to methylated DNA.

In a particular preferred embodiment, the cell content of a subpopulation of cells of interest in determined from the amount of methylated DNA and the total volume or the outer or total surface area of the tissue sample. Thereby it is specific for said subpopulation of cells that one or more cytosines at a defined locus are methylated. In another particular preferred embodiment, the cell content of a subpopulation of cells of interest in determined from the amount of unmethylated DNA and the total volume or the outer or total surface area of the tissue sample. Thereby it is specific for said subpopulation of cells that one or more cytosines at a defined locus are unmethylated. of course, in both embodiments, it is also possibly to consider more than one locus. In this case the results for the amount of methylated DNA and the amount of unmethylated DNA are averaged, respectively. The ratios obtained according to these embodiments are then compared with reference values from which the cell content of the subpopulation of cells of interest in the tissue sample can be deduced.

A preferred embodiment is characterized in that the cell content of said subpopulation of cells is determined by
a) measuring, in one or more loci, the amount of methylated DNA or the amount of unmethylated DNA present in the tissue sample,
b) determining the cell content of said subpopulation of cells of the tissue sample, from the amount of methylated DNA and the total volume or surface area of the tissue sample or from the amount of unmethylated DNA and the total volume or surface area of tissue sample.

In a particular preferred embodiment, the cell content of a subpopulation of cells of interest is deduced from the total DNA yield obtained from a sample. Therefore the total DNA yield is compared with reference values from which the cell content of the subpopulation of cells of interest in the tissue sample can be deduced. According to this embodiment, the total DNA yield is thereby the total amount of DNA which is normalized to the total volume or to the outer or total surface area of the tissue sample. The DNA is thereby isolated and quantified according to standard techniques. Numerous possibilities are known to those skilled in the art. Also sofar unknown methods may be used which are able to determine the total DNA yield.

A preferred embodiment of the invention is characterized in that the cell content of said subpopulation of cells is determined by measuring the total DNA yield of a tissue sample in relation to the total volume or the surface area of the tissue sample.

In a preferred embodiment of the invention the cells of the type of interest are disease-associated cells, wherein disease represents any kind of adverse events. In particular it represents at least one category selected from the group consisting of: undesired drug interactions; cancer diseases; CNS malfunctions; damage or disease; symptoms of aggression or behavioral disturbances; clinical; psychological and social consequences of brain damages; psychotic disturbances and personality disorders; dementia and/or associated syndromes; cardiovascular disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; and headaches or sexual malfunction. In an especially preferred embodiment, the cells of the type of interest are associated with a proliferative disease, in particular with a cancer disease. According to these embodiments, diseased tissue, disease-associated tissue, and/or healthy tissue are taken into account for the determination of the cell content.

In a preferred embodiment of the invention, the cells of said subpopulation of cells are disease-associated cells, preferably cells associated with a proliferative disease, in particular a cancer disease.

In a preferred embodiment, the total DNA methylation level and/or the amount of unmethylated DNA in one or more loci or the amount of methylated DNA in one or more loci is determined by means of bisulfite treatment of the DNA derived from the tissue sample. Numerous methods for bisulfite treatment are known to those skilled in the art. For example, but not limited to please refer to the said above. In a particular preferred embodiment the bisulfite treatment is essentially carried out as described in WO05/038051 (this reference is incorporated by reference in its entirety). Of course other, sofar unknown methods of bisulfite treatment may be used according to the invention as long as the allow a subsequent measurement of the DNA methylation level, the amount of methylated DNA, and/or the amount of unmethylated DNA.

In preferred embodiment, the DNA derived from the tissue sample is bisulfite treated for the measurement of the total DNA methylation level, the measurement of the amount of methylated DNA, and/or the measurement of the amount of unmethylated DNA.

In a preferred embodiment, the total DNA methylation level and/or the amount of unmethylated DNA in one or more loci or the amount of methylated DNA in one or more loci is determined by means of real-time PCR methods into which bisulfite treated DNA is subjected. Several suitable methods are known to those skilled in the art as already described above. Of course, other so far unknown methods which are able to detect DNA methylation quantitatively may be used.

A preferred embodiment of the invention is characterized in that real-time PCR is performed for measurement subsequent to bisulfite treatment.

In a particular preferred embodiment, the total DNA methylation level and/or the amount of unmethylated DNA in one or more loci or the amount of methylated DNA in one or more loci is determined by means of the real-time PCR based methods MethyLight, MethyLight™ ALGO™, or the QM™ assay. These methods are well known to those skilled in the art as already described above. According to this embodiment bisulfite treated DNA is subject to one or more of these methods.

A preferred embodiment of the invention is characterized in that the MethyLight™ method, the MethyLight™ ALGO™ method, or the QM™ assay is performed for measurement subsequent to bisulfite treatment.

In a particular preferred embodiment, the total DNA methylation level and/or the amount of unmethylated DNA in one or more loci or the amount of methylated DNA in one or more loci is determined by means of single nucleotide primer extension, mini-sequencing or sequencing to each of which bisulfite treated DNA is subjected. These methods are well known to those skilled in the art. It is especially preferred that the primer extension is essentially carried out as described in Gonzalgo et al. (Nucleic Acids Research 25(12), 2529-2531, 1997), in U.S. Pat. No. 6,251,594, in WO01/062960, in WO01/062064, or in WO01/62961 (all of these cited references are incorporated by reference to their entirety.

In brief, Gonzalgo et al. (Nucleic Acids Research 25 (12), 2529-2531, 1997), and U.S. Pat. No. 6,251,594 describe each a method for single nucleotide primer extension also known as Ms-SNuPE (both of these cited references are incorporated by reference to their entirety). According to the Ms-SNuPE method, regions of interest are amplified by PCR from bisulfite treated DNA. After purification of the PCR products, primers are proximately hybridized in front of the position to be anaylsed. The primer is then elongated by a single nucleotide either with labeled dCTP or with differently labeled dTTP. In case the cytosine in the original DNA was methylated, then dCTP will be incorporated because methylated cytosines remain unchanged during bisulfite treatment. In the other case, the cytosine in the original DNA was unmethylated, then dTTP will be incorporated because unmethylated cytosine is converted to uracil by bisulfite treatment and subsequent PCR will substitute uracil by thymine. By detection of the different labels, it can be distinguished if a cytosine of a CpG position was methylated or unmethylated. The MS-SNuPE method can also be performed in a quantitative manner.

Alternative methods for primer extension are described in WO01/062960, WO01/062064, or WO01/62961 all of which can be performed in a quantitative manner (all of these cited references are incorporated by reference to their entirety). According to WO01/062960, the primer to be extended hybridises with its 3' terminus complete or only partially onto the positions of interest. A extension of at least one nucleotide occurs only if the primer hybridises completely. WO01/062064 discloses an alternative method in which the primer to be extended hybridises proximately adjacent or at a distance of up to ten bases to the position to be analysed. The primer is then extended by at least a single nucleotide. The third alternative method is described in WO01/62961. According to this method, two set of oligonucleotides are hybridised to the amplified DNA after bisulfite treatment. The first type of oligonucleotide hybridises 5' proximately adjacent or at a distance of up to 10 bases to the position to be analysed. The second type of oligonucleotide hybridises on the amplified DNA so that its 5' terminus hybridises 3' proximately adjacent to said position to be analysed. Through this, the two oligonucleotide are separated from each other by a gap of in the range of 1 to 10 nucleotides. The first type of oligonucleotide is then extended by means of a polymerase, wherein not more than the number of nucleotides lying between the two oligonucleotides are added. Thereby nucleotides are used which comprise differentially labeled dCTP and/or dTTP. The two oligonucleotides are then linked to each other by means of a ligase enzyme. In case the cytosine in the original DNA was methylated, then dCTP will be incorporated. In case the cytosine in the original DNA was unmethylated, then dTTP will be incorporated.

It is further especially preferred that the results of the mini-sequencing or sequencing of bisulfite treated DNA are essentially analysed as described in EP 02090203.7 (hereby incorporated by reference in its entirety). In brief, according to this method the degree of methylation of a cytosine is determined by means of an electropherogram of one or more bases. Thereby the area underneath the electropherogram of a detected base is calculated. The degree of methylation is then deduced by comparison this value for a cytosine position to be analysed with the value obtained for an unmethylated cytosine. For better results, the determination and the consideration of the conversion rate of cytosine to uracil of the bisulfite treatment and/or a standardization of electropherogram signals is favourable.

A preferred embodiment of the invention is characterized in that single nucleotide primer extension, mini-sequencing or sequencing is performed for measurement subsequent to bisulfite treatment.

In a particular preferred embodiment, the total DNA methylation level and/or the amount of unmethylated DNA or the amount of methylated DNA in one or more loci is determined by means of microarray hybridization. Suitable hybridisation methods are well known to those with ordinary skills in the art. Such hybridization methods are described in detail for example in WO01/38565 or WO02/18632 (both of these cited references are incorporated by reference to their entirety).

A preferred method of the invention is characterized in that microarray hybridization is performed for measurement subsequent to bisulfite treatment.

In a particular preferred embodiment, the total DNA methylation level and/or the amount of unmethylated DNA in one or more loci or the amount of methylated DNA in one or more loci is determined by means of methylation specific restriction enzymes. Numerous suitable methods are known to those with ordinary skills in the art. Preferably the Mest evaluation method or the DMH method is carried out. A person will ordinary skills in the art knowns to carry out those methods. For example, but not limited to, the Mest evaluation method is described in detail in DE102004029700 (hereby incorporated by reference in its entirety) and the DMH method is described in Huang et al. (Huang et al., Hum Mol Genet, 8:459-470, 1999), in U.S. Ser. No. 09/497,855, in DE 102005007185.6, in DE102005025 240.0, in DE102005036500.0, or in U.S. 60/710,556 (all of these cited references are incorporated by reference to their entirety). According to these, genomic DNA is fragmented by restriction endonucleases before it is subject to a DNA microarray of cloned CpG islands.

But, in a further preferred embodiment, the DMH method may also include several improvements: After isolation of the DNA, an enrichment of methylated or unmethylated DNA takes place by different means. This means can be one or more of the following: for example restriction endonucleases or proteins, peptides or oligmers which specially bind to CpG dinucleotide either specific on methylated or on non-methylated CpG dinucleotides. Four variants of enrichment by means of restriction endonucleases are especially preferred:

The enrichment by use of only methylation specific restriction enzymes without a previous addition of non-methylation specific restriction enzymes but with a subsequent selective amplification of fragments in the range of 50-5.000 bp via linker (also known as adapters by those skilled in the art). Preferred restriction enzymes are of the group "BisI, BstUI, BshI236I, AccII, BstFNI, McrBC, MvnI, HpaII (HapII), HhaI, AciI, SmaI, HinP1I, HpyCH4IV and mixtures of two or more of the aforesaid enzymes".

Another enrichment is performed by at first, the restriction of DNA by one or more non-methylation specific restriction enzymes; secondly, fragments smaller than 50 bp are discarded and subsequently linker are ligated on each end of every fragment; thirdly, the fragments provided with linker are subject to a restriction by one or more methylation specific restriction enzymes; and fourthly, the resulted fragments are subjected to an amplification, wherein only fragments are amplified which are not restricted in step three. According to this procedure fragments of 50-5.000 bp are enriched. It is thereby preferably that three different methylation specific restriction enzymes are used, one or more of the methylation specific restriction enzymes have a restriction site in the length of 4 bp, in particular which do not contain any CG. The non-methylation specific restriction enzymes are selected from the group "MseI, BfaI, Csp6I, Tru1I, Tvu1I, Tru9I, Tvu9I, MaeI, XspI and mixtures of two or more of the aforesaid enzymes". Preferably a mixture of MseI, BfaI and Csp6I is used. The methylation specific restriction enzymes can be any enzyme which either cuts methylation specifically unmethylated or methylated DNA. Preferably the methylation specific enzyme is selected from the group of "BisI, BstUI, BshI236I, AccII, BstFNI, McrBC, MvnI, HpaII (HapII), HhaI, AciI, SmaI, HinP1I, HpyCH4IV, EagI and mixtures of two or more of the aforesaid enzymes". In particular the use of BstUI, HpaII, HpyCH4IV and HinP1I is preferred.

Besides that, an enrichment is also possible according to the method of "NotI representation" as exemplified in WO02/086163 (hereby incorporated by reference in its entirety). According to this, DNA is restricted by suitable enzymes like BamHI of Bg1II. After inactivation of the enzymes, the fragments are circularized by self ligation, before they are subject to another restriction by NotI which only cut its unmethylated recognition side. Through this, fragments with only unmethylated NotI recognition sites are linearised onto which specific linker are ligated. Therefore it is possible to amplify those fragments. In principle this method can also be adjusted to other methylation specific restriction enzymes as listed above.

As the fourth procedure of enrichment by the means of restriction endonucleases, the MS AP-PCR (Methylation Sensitive Arbitrarily-Primed Polymerase Chain Reaction) is preferred. This technique is well known in the art and was described the first time by Gonzalgo et al., Cancer Res., 57:594-599, 1997 (hereby incorporated by reference in its entirety). In principle, genomic DNA is subject to an restriction digestion, for example HpaII. The resulting fragments are then subject to an amplification wherein random primers are used which are rich in CG dinucleotides. According to this, DNA regions are amplified which are rich in CG dinucleotides.

An enrichment of methylated or non-methylated DNA can also occur by means of proteins, peptides or oligmers which specifically bind to methylated or non-methylated DNA. The binding can be sequence specific or unspecific. However, unbound DNA is separated by bound DNA through the binding. Depending on which kind of DNA is of interest, methylated or non-methylated DNA, or which kind of DNA is bound, the bound or unbound DNA fraction is further analysed. These means proteins may be used which specifically bind unmethylated DNA, as well as proteins which specifically bind methylated DNA. Furthermore, it is possible to bind that DNA, which is later analysed. Therefore the unbound DNA is removed before the bound DNA is released from the protein. On the other hand it is also possible to let bind the background DNA to the proteins and thereby it is removed from the reaction mixture. Of course, it is also possible to carry out such an enrichment in two subsequent steps whereby the order is not relevant. In one step, proteins which specifically bind unmethylated DNA and in the other step, proteins which specifically bind methylated DNA are used. Such a proceeding has the advantage that simultaneously unmethylated DNA and methylated DNA are enriched while DNA with no or only a view CpG positions is removed.

An enrichment can be achieved by proteins which methylation specifically bind to DNA and also by the use of their domains or peptides. Such proteins can be for example MeCP2, MBD1, MBD2, MBD4 and Kaiso. The later binds sequence specifically namely on symmetrical methylated CpGpCpG positions. Exemplary the Methyl-CpG-binding domain of MeCP2 protein or the CXXC-3 domain of the MBD1 protein is mentioned as suitable domains for enrichment (for an overview: Shiraishi et al., Anal Biochem. 2004 Jun. 1; 329 (1):1-10; Hendrich and Tweedie, Trends Genet. 2003 May, 19 (5): 269-77; Jørgensen et al., Molecular and Cellular Biology, 2004, 3387-3395; all of these cited references are incorporated by reference to their entirety).

Typically, the proteins, domains or peptides are bound to a solid surface for example on beads which enable a separation of by means of a batch procedure or by a column chromatography (Cross et al., Nature Genetics, 1994 (6) 236-244; Shiraishi et al., Anal Biochem. 2004 Jun. 1; 329 (1):1-10; both of these cited references are incorporated by reference to their entirety). Biochemical methods which have to be applied are known to those skilled in the art. This may for example include the use of biotin or histidine tags (for example Gretch et al., Anal Bio-chem., 1987, (163) 270-7; Janknecht et al., Prc Nat. Acad Sci, 1991, (88) 8972-6; both of these cited references are incorporated by reference to their entirety).

Moreover, an enrichment can also be achieved by methylation specific antibodies for example by means of the anti 5-methylcytosine antibody available from Abcam Inc. Again the enrichment can be performed in a batch procedure or by column chromatography. Details are known to persons skilled in the art (for example: Fisher et al., Nucleic Acids Res. 2004, 32(1), 287-97; hereby incorporated by reference in its entirety). On the hand, an enrichment can also be achieved by immunoprecipitation with methylation specific antibodies and suitable secondary antibodies, followed by a proteinase K treatment.

Another variant of enrichment is the chromatin immunoprecipitation (ChIP). Details are known to those skilled in the art (for example: Matarazzo et al., Biotechniques, 2004, 37(4), 666-8, 670, 672-3.; hereby incorporated by reference in its entirety). According to this, a immunoprecipitation is carried out with antibodies which are specific for 5-methylcytosine binding proteins like MeCP2, MBD1, MBD2, MBD4 or Kaiso. Thereby the proteins are fixed onto the DNA before the antibodies are added. In particular it is preferred to purify the DNA first and then add the DNA binding proteins. It is also particularly preferred to apply a suitable physical method like ultracentrifugation before the second precipitation step. A suitable kit is available from Panomics, Inc.

Furthermore, an enrichment can be achieved by triplex binding oligomers, which can PNA- or DNA-Oligomers. This method is described in detail in WO04/113564 (hereby incorporated by reference in its entirety). In principle, a triplex-bilding oligomer is brought in contact with DNA. Thereafter it preferentially forms a triple helix with unmethylated DNA in comparison to methylated DNA. From this advantage is taken for enrichment.

In principle, a DNA may be fragmentated randomly or non-randomly before it is subject to enrichment by any method using proteins, peptides or oligmers. This is done as it is known by those skilled in the art. Fragmentation can be performed randomly for example with sonification or shearing. But is also can be performed non-randomly, preferentially by the use of methylation specific restriction endonucleases, in particular of the group of "BisI, BstUI, BshI236I, AccII, BstFNI, McrBC, MvnI, HpaII (HapII), HhaI, AciI, SmaI, HinP1I, HpyCH4IV and any mixture of two or more of the aforesaid enzymes".

A further reduction of complexity can be achieved by physical methods which are applied before or after an amplification. Such physical methods can for example be gel electrophoresis, size-exclusion chromatography or filtration.

After enrichment of the DNA, the fragments are labelled preferentially with a suitable fluorescent dye. Such a dye enables selective one or two dimensional scanning. Typically Cy3 and/or Cy5 are used as dyes. But also other suitable dyes are known to those skilled in the art. Furthermore, it is preferred that the fragments are labelled with biotin, which interacts with another substance in the actually detection process. Thereby it is necessary to carry out two arrays which are compared with each other.

The labelling is carried out preferentially by means of an amplification, in particular whole genome amplifications. Several suitable methods are known by those skilled in the art.

The labelled fragments are then subject to a DNA microarray which can be either a array of cloned CpG islands or array of oligonucleotides. The oligonucleotides of the oligonucleotide microarray can be any oligonucleotide suitable for the detection of methylation or non-methylation of CpG dinucleotides. Preferably the oligonucleotides are design after fragments derived according to the following two strategies:

According to the first strategy, A) the genome of an organism of desire is analysed for first fragments, which are flanked by recognition sites of non-methylation specific restriction enzymes of interest and which are in the range of 100-1.200 bp. B) Second fragments are then selected under those first fragments which have no more than 50%, preferably no more than 20% of repeats. These two steps A) and B) can be performed in arbitrary order. Additionally, C) the second selected fragments are analysed for the presence of recognition sites of methylation specific restriction endonucleases of interest. Those second fragments which include such a recognition site are then selected as third fragments. Again, the steps A), B) and C) can be performed in arbitrary order.

According to the second strategy, A) the genome of an organism of desire is analysed for first fragments, which are flanked by recognition sites of methylation specific restriction enzymes of interest and which are in the range of 100-1.200 bp. B) Second fragments are then selected under those first fragments which have no more than 50%, preferably no more than 20% of repeats. C) The second selected fragments are analysed for the presence of recognition sites of methylation specific restriction endonucleases of interest. Those second fragments which include such a recognition site are then selected as third fragments. Again, the steps A), B) and C) can be performed in arbitrary order.

According to the third strategy, A) the genome of an organism is tested for first partial sequences, which are limited by cutting sites of one or several of the first used restriction enzymes and have a length of 100 to 1,200 base pairs, and said first partial sequences are selected, B) such partial sequences are excluded from the first partial sequences, which comprise more than 50% repeats—it is preferred, if such partial sequences are excluded, which contain more than 20% repeats, thereby a group of second partial sequences being formed, and the steps A) and B) can be performed in any order, C) the selected second partial sequences are tested for cutting sites of the restriction enzymes used secondly, and as third partial sequences those second partial sequences are selected, which contain such cutting sites, and the steps A) to C) can be performed in any order.

Fragments selected according to these strategies can match fragments obtained by the enrichment procedures. The sequence of the oligonucleotides of the array is chosen from the selected fragments, so that they would hybridise to the selected fragments or so that they are identical to them and therefore would hybridise to the counter strand. These oligonucleotides are then synthesised on the array or are linked to it after the synthesis. Typically 3-30 oligonucleotides are derived from one fragment, whereby it is possible that the oligonucleotide sequences are overlapping. Preferably the oligonucleotides have a defined distance between each other so that a so called "tiling array" results, similar as described by Kapranov et al., Science, 2002, 296(5569):916-9; hereby incorporated by reference in its entirety).

According to the DMH method, fragments hybridized on the immobilized oligonucleotides contain preferably nucleic acid sequences, which methylation positions are non-methylated or methylated in case of a definite disease in comparison to the normal condition. The oligonucleotides do not have to necessarily encode for the methylation positions by themselves, although it is possible. Moreover, it is possible that a oligonucleotide array carries different sets of oligonucleotides, suitable for the detection of different diseases or of predispositions for a disease or of the susceptibility for side effects for a definitive medical treatment. Additionally, it is also possible to predict the type, the aggressiveness or the progression of a disease or for the effectiveness of a medical treatment, in case it is based on methylation differences. Further conclusions can be made by comparison of the results obtained by means of an oligonucleotide array according to the DMH method with a results obtained with arrays with different oligonucleotide set, for example oligonucleotide sets suitable for SNP analysis.

A preferred embodiment of the invention is characterized in that the total DNA methylation level, the amount of methylated DNA, and/or the amount of unmethylated is measured using methylation specific restriction enzymes, preferably the Mest evaluation method or the DMH method.

Of course, also so far unknown methods may also used for the determination of the total DNA methylation level and/or the amount of unmethylated DNA or the amount of methylated DNA in one or more loci.

A preferred embodiment of the invention is a method for diagnosing a condition or a disease. The condition or disease is thereby characterized by methylation levels at one or more CpG dinucleotides, the levels and positions are specific for said condition or disease. Furthermore this embodiment comprises, a) obtaining a tissue sample with disease-associated cells, b) determining the content of the disease-associated cells within said tissue sample, c) measuring the methylation levels at one or more CpG dinucleotides within the disease-associated cells from the total DNA methylation level and the disease-associated cell content, and e) comparing said methylation level at one or more CpG dinucleotides within the disease-associated cells to a corresponding reference value.

A preferred embodiment of the invention is method for diagnosing a condition or disease, characterized by specific methylation levels of one or more methylation variable genomic DNA positions in a disease-associated cell of a tissue sample, comprising:
a) obtaining a tissue sample comprising genomic DNA having one or more methylation variable positions in one or more regions thereof,
b) determining the disease-associated cell content within the tissue sample in a quantitative or semi-quantitative manner,
c) measuring the total DNA methylation level of one or more methylation variable genomic DNA positions of the tissue sample,
d) determining the DNA methylation level of one or more methylation variable genomic DNA positions within the disease-associated cells from the total DNA methylation level and the disease-associated cell content,
e) comparing said methylation level to that of corresponding reference tissue.

Another preferred embodiment is a method for predicting treatment response or prognosis of disease for an individual. The treatment response, the disease and/or the health status of the individual are characterized by methylation levels at one or more CpG dinucleotides, the levels and methylation positions are hereby specific for said treatment response, disease or health status. In addition, this embodiment comprises, a) obtaining a tissue sample with disease-associated cells from said individual, b) determining the content of the disease-associated cells within said tissue sample, c) measuring the methylation levels at one or more CpG dinucleotides within the disease-associated cells from the total DNA methylation level and the disease-associated cell content, and e) comparing the methylation level at one or more CpG dinucleotides specific for the health status of the individual to a corresponding reference value which is specific for the treatment response or the disease.

A preferred embodiment of the invention is a method for predicting treatment response or prognosis of disease for an individual, characterized by specific methylation levels of one or more methylation variable genomic DNA positions in a disease-associated cell of a tissue sample, comprising:
a) obtaining a tissue sample comprising genomic DNA having one or more methylation variable positions in one or more regions thereof,
b) determining the disease-associated cell content within the tissue sample in a quantitative or semi-quantitative manner,
c) measuring the total DNA methylation level of one or more methylation variable genomic DNA positions of the tissue sample,
d) determining the DNA methylation level of one or more methylation variable genomic DNA positions within the disease-associated cells from the total DNA methylation level and the disease-associated cell content,
e) comparing said methylation level to that of corresponding reference tissue.

Subject of the present invention is also kit, comprising
a) reagents for quantitative or semiquantitative determination of the cell content of a subpopulation of cells within a tissue sample,
b) reagents for measuring the total DNA methylation level of one or more specific CpG positions of said subpopulation of cells within the tissue sample, and
c) a container.

Preferably, a kit according to the invention comprises
a container.
one or more reagents for quantitative or semiquantitative determination of the cell content of a subpopulation of cells of interest within a tissue sample. Said reagent may be any substance, solution or device which is suitable for the above said determination of the cell content according by means of histopathology, staining or specific antibodies. Suitable substances, solutions, or devices are well known to those skilled in the art. Furthermore, the said reagent may be any substance, solution or device suitable for carrying out a expression analysis as said above. Suitable substances, solutions, or devices are well known to those skilled in the art. In addition, the said reagent may also be any substance, solution or device suitable for carrying out a DNA methylation analysis, in particular by means of bisulfite treatment, the MethyLight™ method, the MethyLight™ ALGO™ method, the QM™ assay, nucleotide primer extension, mini-sequencing, sequencing, hybridisation on DNA microarrays, hybridisation on oligomer arrays, methylation-specific restriction enzymes, the Mest evaluation method, the DMH method, or all of the aforesaid or only parts thereof as said above. Suitable substances, solutions, or devices are well known to those skilled in the art.
one or more reagents for the quantification of the total DNA methylation level at one or more specific CpG positions within the cells of a subpopulation of cells of interest. Said reagent may be any substance, solution or device for carrying out the DNA methylation analysis as it was already mentioned above.

Another preferred kit comprises, in addition, instructions or algorithms for carrying out the method of the invention. Such kind of instructions or algorithms may comprise information how to determine the methylation level within cells of a subpopulation of a given tissue sample.

In addition, a preferred kit of the invention comprises
a) reagents for quantitative or semiquantitative determination of the cell content of a subpopulation of cells within a tissue sample
b) reagents for measuring the total DNA methylation level of one or more specific CpG positions of said subpopulation of cells within the tissue sample,
c) a container, and
d) operator instructions and/or algorithms to determine the methylation level within the cells of a subpopulation of cells of a given sample.

A particular preferred kit comprises furthermore one or more of the following
a) one or more solution and/or reagent for histological and/or immunological analysis,
b) one or more primer and/or solution for DNA amplification, and
c) one or more primer, oligonucleotide and/or solution for detection of the DNA methylation level and/or the detection of the amount of methylated and/or unmethylated DNA.

Another preferred kit of invention comprises one or more of the following:
a container,
one or more primer suitable for the amplification of a subpopulation of cells specific DNA methylation marker to determine the cell content of said subpopulation of cells,
one or more primer suitable for the amplification of one or more fragments to determine the DNA methylation level of one or more specific CpG positions within the total DNA, and
operator instructions and/or algorithms to determine the methylation level within the tumor cells of a given sample.

Preferably, the said kits are kits suitable for conducting a method or an embodiment of the invention.

The embodiments and kits disclosed herein are preferably used for the analysis, characterization, classification, differentiation, grading, or staging of cells or combinations thereof. Preferably these cells are disease associated, in particular these cells are tumor cells. From such an analysis, characterization, classification, differentiation, grading, staging or combinations thereof a person with ordinary skills in the art can deduce an analysis, characterization, classification, differentiation, grading, staging or combinations thereof from a diseased tissue. A person with ordinary skills in the will then be able to diagnose a proliferative disorder, a predisposition to such a proliferative disorder or a combination of both.

Preferably, the methods and kits described herein are used for analysis, characterization, classification, differentiation, grading, staging of a cell or tissue, diagnosis of proliferative disorders, diagnosis of the predisposition to proliferative disorders, or combinations thereof.

Of course, in the same manner also indication-specific targets can be identified which are specific for a predisposition for a disease or which are specific for a progression of a disease.

The use according to one or more of the embodiments or of a kit according to the invention is preferred for identifying an indication-specific target, wherein
a) the DNA methylation level in disease-associated cells of a subpopulation of cells within a tissue sample is determined,
b) the DNA methylation level in corresponding healthy cells is determined; and
c) a indication-specific target is defined based on differences in the DNA methylation level of the DNA derived from the disease-associated cells in comparison to the DNA derived from the corresponding healthy cells.

The use of the methods or kits described herein is preferred if the indication-specific target is a protein, peptide, RNA or any other endogenous bioactive substance as for example a hormon.

The use is preferred if the indication specific target is a protein, peptide or RNA.

In particular, a use is preferred wherein a per se known modulator of the protein, peptide or RNA is assigned to the specific indication of the diseased tissue.

Furthermore, the use of such a modulator is particularly preferred for preparing a pharmaceutical composition in case of a specific indication. This is especially preferred if the specific indication is a specific cancer indication.

In particular, the use of the modulator assigned to the specific indication of the diseased tissue is preferred for preparing a pharmaceutical composition with a specific indication, in particular a specific cancer indication.

The methods and kits disclosed herein are preferable used for diagnosis, prognosis or both of adverse events of patients or individuals. Thereby diagnosis means diagnose of a adverse event, a predisposition for an adverse event and/or a progression of a adverse events. Furthermore prognosis means prognose of a adverse event, a predisposition for a adverse event and/or a progression of a adverse events. These adverse events belong at least to one of the following categories: undesired drug interactions; cancer diseases; CNS malfunctions; damage or disease; symptoms of aggression or behavioral disturbances; clinical; psychological and social consequences of brain damages; psychotic disturbances and personality disorders; dementia and/or associated syndromes; cardiovascular disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; and headaches or sexual malfunction.

The methods and test kits disclosed herein are also preferably used for distinguishing subpopulations of cells, tissues or for investigating cell differentiation. In a preferred embodiment, this information may be used for analysing the response of a patient to a drug treatment. All cited references are hereby incorporated by reference in their entirety.

Example 1

Methylation Markers Analysis of Biological Samples Comprising Lung Cancer

The aim of the present example was to establish that the method according to the present invention was suitable for analysis of biological samples in order to quantify the amount of cancer cells. Lung cancer was selected as a first case study.

In order to quantifying the amount of lung cancer cells in a biological sample, as relative to the amount of normal lung cells according to the method of the present invention it was first necessary to determine methylation markers suitable for differentiating between normal lung tissue and lung cancer tissue, wherein said lung cancer tissue is not contaminated by other cell types. Accordingly lung cancer cell lines were used as immortalized cell lines are solely comprised of proliferating cells do not comprise normal tissues. Furthermore in order to confirm that the selected methylation markers were heterogeneously methylated in lung cancer samples, the methylation patterns thereof were also determined in biopsy samples from lung cancer patients.

Suitable methylation markers were identified by means of a differential methylation hybridisation investigation of lung normal tissue, lung cancer cell lines & lung cancer biopsy. Differential methylation hybridisation was carried out substantially as described by Huang et al., Hum Mol Genet, 8 (3): 459-470 (1999).

Samples 20 tissue samples from healthy lung, 22 surgically removed lung cancer samples and 9 lung cancer cell lines (taken from the NCBI 60 panel of cell lines) were analysed. The surgically removed lung cancer samples had previously been assessed by a pathologist to determine % tumour content of the sample.

Furthermore, artificially ss1 methylated (100% methylation) DNA and commercially available unmethylated genomic DNA (0% methylation) DNA were also analysed as controls. This enabled calibration of the results.

Differential Methylation Hybridisation

DNA Isolation

Genomic DNA was isolated by means of the QIAamp DNA Mini Kit (Qiagen, Hilden, Germany) in accordance with the manufacturer's instructions.

2: Generation of DNA-Microarrays with Oligonucleotides.

A whole genome DNA microarray was designed by in-silico analysis of the Ensembl Human Genome database to determine restriction fragments by digestion with selected restriction enzymes, both methylation specific and non-methylation specific.

A subset of the possible restriction fragments was then selected using criteria that included but were not limited to fragment size, repeat content.

Said selected subset of fragments was then synthesised on a microarray surface according to conventional means.

3: Restriction Digest of the DNA Samples.

The genomic DNA was prepared for hybridisation to the microarray.

Genomic DNA of each sample was first digested with non-methylation specific restriction enzymes MseI, Bfa1 and Csp6 (obtainable from New England Biolab and MBI Fermentas) according to the manufacturer's instructions. Purification was then performed with the QuiaQuick PCR product purification column kit (Quiagen, Hilden, Germany). Fragments shorter than 40 bases were rejected according to the manufacturers information. However it cannot be excluded that larger fragments up to a size of about 100 bp also rejected. Subsequently, the ligation of adapters (or linkers) was performed according to the procedure described by Huang et al., Hum Mol Genet, 8 (3): 459-470 (1999). After this, the purified ligated DNA was digested with 10 units each of the methylation sensitive (i.e. methylation specific) restriction enzymes BstU1, Hap II, HpyCH4IV and HinP1 (obtainable from New England Biolabs) according to the manufacturers instructions.

About 10-100 ng of the methylation sensitive digested DNA was used for a PCR reaction, which amplifies unrestricted DNA fragments in the range of 50-1000 bp. The amplified DNA was purified by means of the QuiaQuick PCR product purification kit (Qiagen, Hilden, Germany).

The purified PCR products were fragmented and labeled according to the specifications of the "Gene Chip Mapping Assay Manual" of Affymetrix Inc., in particular Chapter 4 (pages 38-42).

4: Hybridisation of samples on the DNA microarray

The amplificates hybridised to the DNA microarray synthesised as above. The hybridisation and detection was carried out according to the instructions in "Gene Chip Mapping Assay Manual" by Affymetrix Inc., in particular chapter 5 (page 69-70), as well as chapter 6 "Washing, Staining & Scanning" (page 75-92).

Each sample thereby generated an individual hybridisation pattern, from which methylation differences between the three sample types could be deduced by determining DNA fragment sequences which show differential hybridisation signals between samples of the compared tissues.

Results

Figure 2:
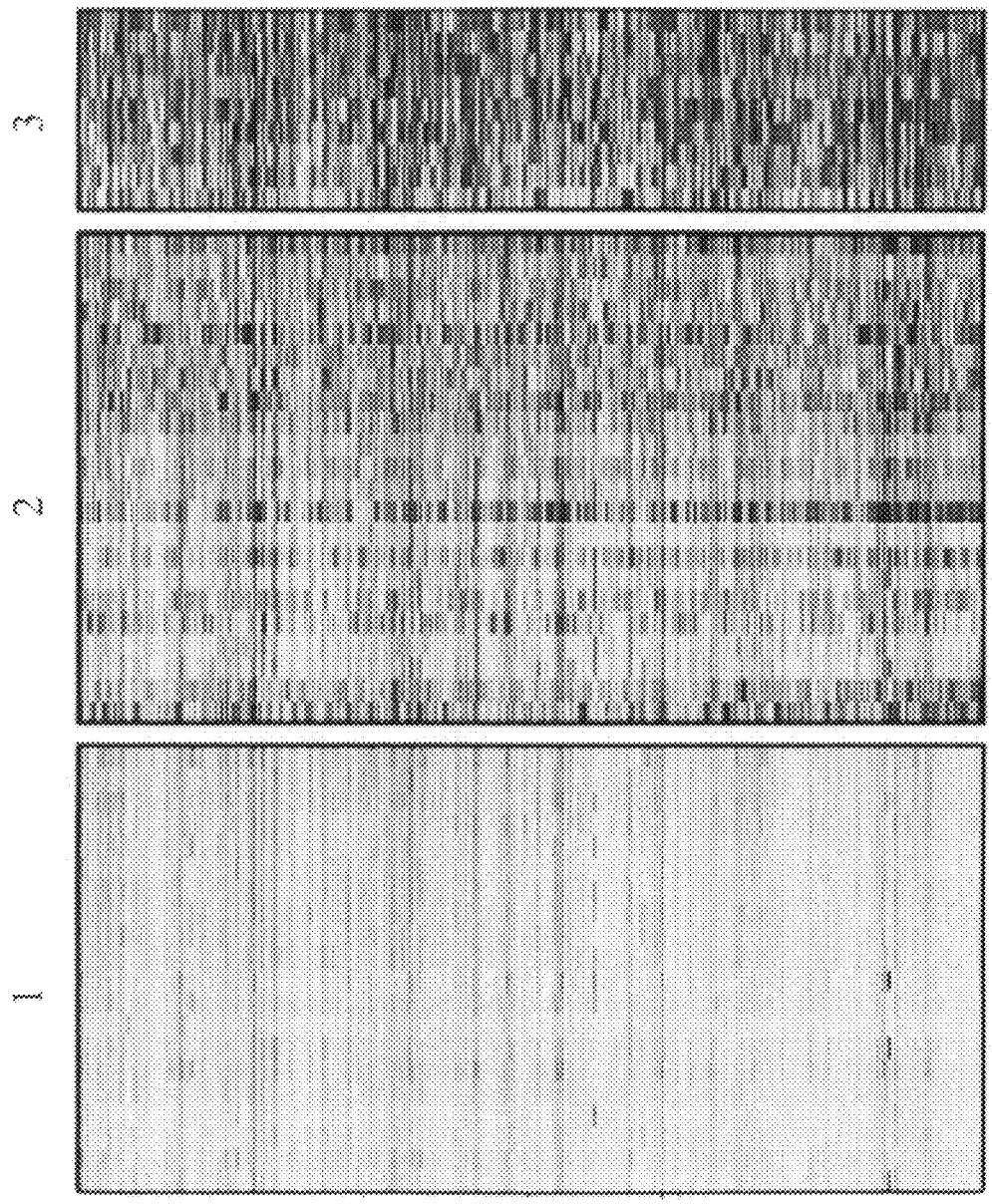

FIGS. 1 and 2 together provide an overview of the relative methylation of approximately 1,000 fragments of the DMH chip.

Each column of the matrices represent the DMH methylation data for one sample. Each row of a matrix represents a DMH fragment and each column represents an individual DNA sample. The degree of methylation represented by the shade of each position within the column from black representing 100% methylation to light grey representing 0% methylation. The degree of methylation was determined by calibration to the 0% and 100% methylated controls. Fragments are ranked in the matrix according to the difference in average methylation between the normal and lung cancer tissue (not cell line) groups.

Based on a threshold of 25% methylation difference 497 fragments were identified which were generally hyper-methylated in cell lines (FIG. 1), and 556 that were generally hypomethylated in cell lines (FIG. 2). In FIG. 1 fragments with the highest difference in average methylation between the normal and lung cancer tissue (not cell line) groups are listed at the top of the matrix. In FIG. 2 fragments with the highest difference in average methylation between the normal and lung cancer tissue (not cell line) groups are listed at the bottom of the matrix.

In each of FIGS. 1 and 2 the different groups of samples are presented in a discreet block. "A" indicates normal tissue, "B" indicates surgically removed lung cancer samples and "C" indicates lung cancer cell lines.

Figure 3:
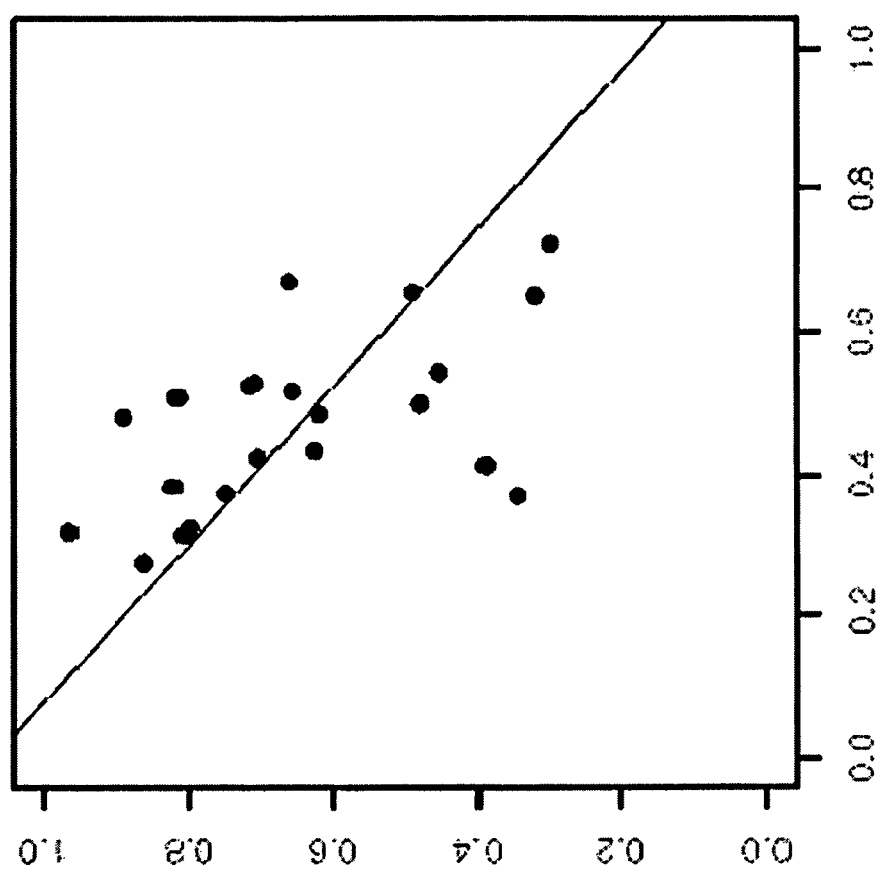
FIG. 3 provides a plot of the average methylation of 20 DMH fragments (SEQ ID NO: 21 to SEQ ID NO: 40) which are hypermethylated in lung cancer cell lines (X-axis), against 20 DMH fragments (SEQ ID NO: 1 to SEQ ID NO: 20) which are hypomethylated in lung cancer cell lines (Y-axis) as measured in 20 surgically removed lung cancer samples according to Example 1.

It can be seen that many fragments are capable of differentiating between lung normal tissue and lung cancer cell lines such that they are substantially 100% methylated in one class and substantially 0% methylated in the other class. It can be further concluded that the surgically removed lung cancer samples generally present with a mixed degree of methylation as compared to the cell lines. Accordingly 40 markers were selected, namely the lower 20 markers which were hypomethylated in cell lines from FIG. 2 (referred to in FIG. 3 as "hypomethylated"), and the first 20 markers which were hypermethylated in lung cell lines and hypomethylated in lung normal tissues from FIG. 1 (referred to in FIG. 3 as "hypomethylated"). The sequence of each of said genomic nucleic acid fragment is provided in the sequence listing. SEQ ID NO: 1 to SEQ ID NO: 20 provide the sequences of the markers which were hypomethylated in cell lines. SEQ ID NO: 21 to SEQ ID NO: 40 provide the sequences of the markers which were hypermethylated in cell lines. 20 of the surgically removed lung cancer samples were then selected. For each of the samples the average quantified methylation of the 20 fragments in each of the hypomethylated and hypermethylated groups was determined. The average of the each was then plotted against each other, as shown in FIG. 3. The correlation of the plot was −0.571.

Figure 4:
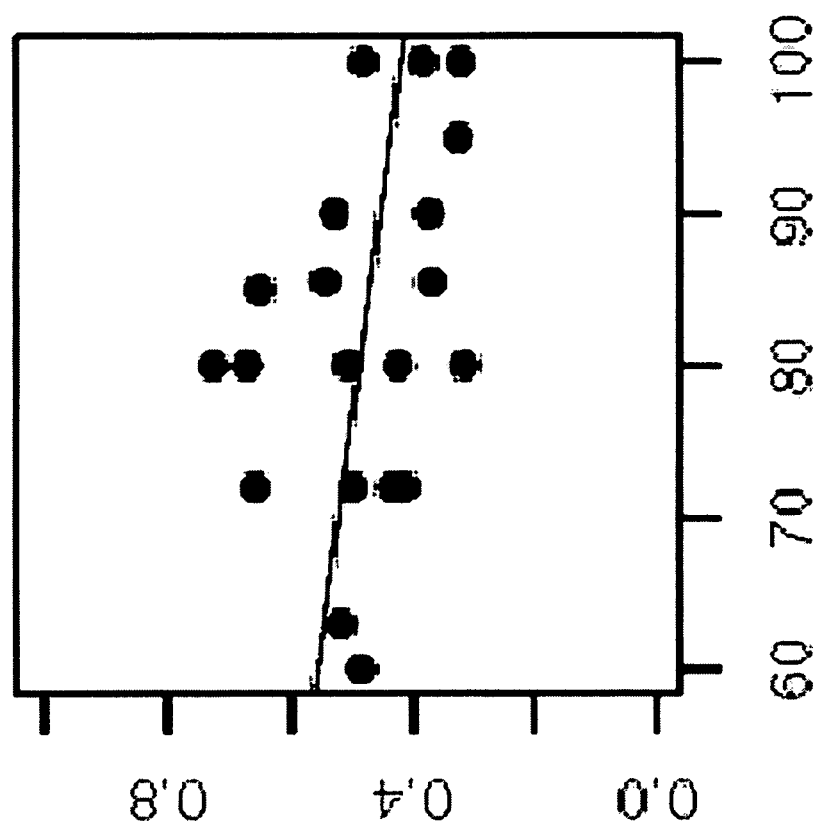
FIG. 4 provides a plot of the pathologist estimated % tumour content (X-axis), against average methylation of 20 DMH fragments (SEQ ID NO: 1 to SEQ ID NO: 20) which are hypomethylated in lung cancer cell lines (Y-axis) as measured in 20 surgically removed lung cancer samples according to Example 1.
Figure 5:
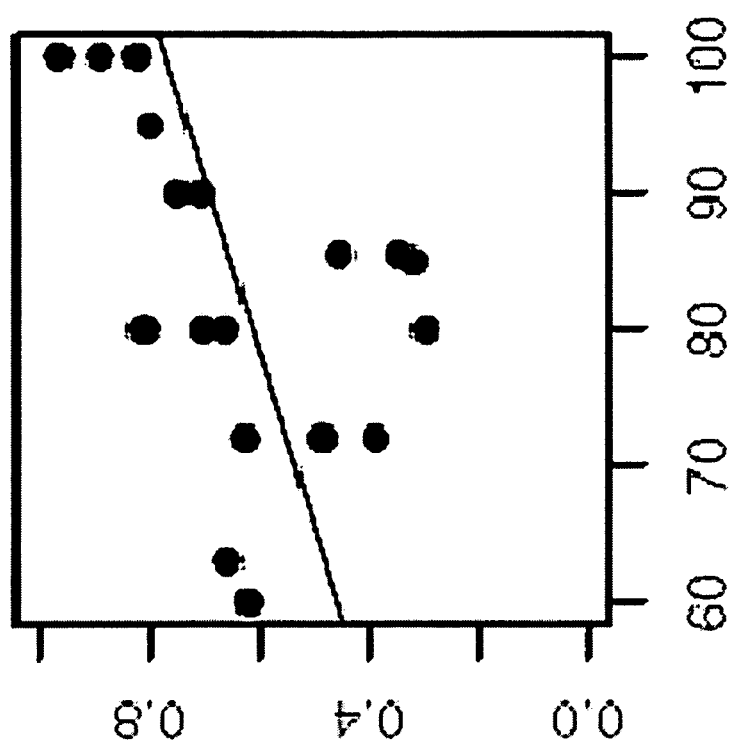
FIG. 5 provides a plot of the pathologist estimated % tumour content (X-axis), against average methylation of 20 DMH fragments (SEQ ID NO: 21 to SEQ ID NO: 40) which are hypermethylated in lung cancer cell lines (Y-axis) as measured in 20 surgically removed lung cancer samples according to Example 1.

The methylation average methylation values of the hypo- and hyper-methylated groups of fragments was then plotted against the tumour cell content of each sample, as estimated by a pathologist. FIG. 4 shows the plot of hypomethylated average against % tumour cell content, the correlation of the plot was −0.329. FIG. 5 shows the plot of hypomethylated average against % tumour cell content, the correlation of the plot was −0.456.

The invention claimed is:

1. Method for the determination of the DNA methylation level of one or more specific CpG positions of a subpopulation of cells within a tissue sample comprising a plurality of subpopulations of cells, comprising
    a) determining, in a quantitative or semi-quantitative manner, the proportion of cells within said tissue sample represented by said subpopulation of cells,
    b) measuring the total DNA methylation level of said one or more specific CpG positions within said tissue sample,
    c) determining the DNA methylation level within the cells of said subpopulation of cells based on the total DNA methylation level of said one or more specific CpG positions within the tissue sample and the proportion of cells within said tissue sample represented by said subpopulation.

2. Method according to claim 1, characterized in that the cell content of said subpopulation of cells is determined by using staining methods or specific antibodies.

3. Method according to claim 1, characterized in that the proportion of cells of said subpopulation of cells is determined by histopathology.

4. Method according to claim 1, characterized in that the cell content of said subpopulation of cells is determined by using expression analysis.

5. Method according to claim 1, characterized in that the cell content of said subpopulation of cells is determined by DNA methylation analysis.

6. Method according to claim 5, characterized in that the cell content of said subpopulation of cells is determined by
    a) measuring, in one or more loci, the total DNA amount present in the tissue sample,
    b) measuring, in one or more loci, the amount of methylated DNA,
    c) determining the cell content of said subpopulation of cells in the tissue sample, as the amount of methylated DNA within the total DNA.

7. Method according to claim 5, characterized in that the cell content of said subpopulation of cells is determined by
    a) measuring, in one or more loci, the total DNA amount present in the tissue sample,
    b) measuring, in one or more loci, the amount of unmethylated DNA, and
    c) determining the cell content of said subpopulation of cells in the tissue sample, as the amount of unmethylated DNA within the total DNA.

8. Method according to claim 5, characterized in that the cell content of said subpopulation of cells is determined by
    a) measuring, in one or more loci, the unmethylated DNA amount present in the tissue sample,
    b) measuring, in one or more of said loci, the methylated DNA amount present in the tissue sample, and
    c) determining the cell content of said subpopulation of cells of the tissue sample as the ratio of methylated DNA to unmethylated plus methylated DNA, or as the ratio of unmethylated DNA to unmethylated plus methylated DNA.

9. Method according to claim 5, characterized in that the cell content of said subpopulation of cells is determined by
    a) measuring, in one or more loci, the ratio of methylated DNA to unmethylated DNA present in the tissue sample, or by measuring, in one or more loci, the ratio of unmethylated DNA to methylated DNA present in the tissue sample, and
    b) determining the cell content of said subpopulation of cells of the tissue sample from the ratio of methylated DNA to unmethylated DNA, or from the ratio of unmethylated DNA to methylated DNA.

10. Method according to claim 5, characterized in that the cell content of said subpopulation of cells is determined by
    a) measuring, in one or more loci, the amount of methylated DNA or the amount of unmethylated DNA present in the tissue sample,
    b) determining the cell content of said subpopulation of cells of the tissue sample, from the amount of methylated DNA and the total volume or surface area of the tissue sample or from the amount of unmethylated DNA and the total volume or surface area of tissue sample.

11. Method according to claim 1, characterized in that cell content of said subpopulation of cells is determined by measuring the total DNA yield of a tissue sample in relation to the total volume or surface area of the tissue sample.

12. Method according to claim 1, wherein the cells of said subpopulation of cells are cells associated with a cancer.

13. Method according to claim 1, wherein DNA derived from the tissue sample is bisulfite treated for the measurement of the total DNA methylation level, the measurement of the amount of methylated DNA, and/or the measurement of the amount of unmethylated DNA.

14. Method according to claim 13, characterized in that real-time PCR is performed for measurement subsequent to bisulfite treatment.

15. Method according to claim 13, characterized in that single nucleotide primer extension, mini-sequencing or sequencing is performed for measurement subsequent to bisulfite treatment.

16. Method according to claim 1, characterized in that microarray hybridization is performed for measurement subsequent to bisulfite treatment.

17. Method according to claim 1, characterized in that the total DNA methylation level, the amount of methylated DNA, and/or the amount of unmethylated is measured using methylation specific restriction enzymes, preferably the Mest evaluation method or the DMH method.

* * * * *